United States Patent
Singh et al.

(10) Patent No.: US 6,652,860 B1
(45) Date of Patent: Nov. 25, 2003

(54) PEPTIDE, APOEP 1.B, COMPOSITIONS AND USES THEREOF

(75) Inventors: Bhagirath Singh, London (CA); Beverley Rider, Palo Alto, CA (US)

(73) Assignee: University of Western Ontario, London (CA)

( * ) Notice: Subject to any disclaimer, the term of this patent is extended or adjusted under 35 U.S.C. 154(b) by 0 days.

(21) Appl. No.: 09/581,153

(22) PCT Filed: Dec. 11, 1998

(86) PCT No.: PCT/CA98/01129

§ 371 (c)(1),
(2), (4) Date: Aug. 7, 2000

(87) PCT Pub. No.: WO99/31227

PCT Pub. Date: Jun. 24, 1999

Related U.S. Application Data

(60) Provisional application No. 60/069,531, filed on Dec. 12, 1997.

(51) Int. Cl.[7] ................ A61K 38/00; A61K 38/04; A61K 39/100; A01N 43/04; C07K 1/00
(52) U.S. Cl. .................. 424/185.1; 514/14; 514/44; 514/21; 514/406; 514/2; 536/23.1; 536/23.5; 530/300; 530/327; 530/359
(58) Field of Search .................. 530/324, 359, 530/327, 300; 514/56, 150, 553, 59, 367, 369, 576, 470, 14, 44, 2, 21, 406; 435/11, 212; 424/78, 185.1; 536/23.1, 23.5

(56) References Cited

U.S. PATENT DOCUMENTS 5,116,739 A     5/1992  Teranishi et al.

OTHER PUBLICATIONS

A von Rohr et al., Progress in Growth Factor Research, "Clinical Applications of Interleukin–2," 1992, vol. 4, pp. 229–246.*

BJ Rider et al., Molecular Immunology, "Immune Responses to Self Peptides Naturally Presented by Murine Class II Major Histocompatibility Complex Molecules," 1996, vol. 33, No. 7/8, pp. 625–633.*

Hunt, Donald F. et al., Science, vol. 256, 1817–1820, 1992.

* cited by examiner

Primary Examiner—David Guzo
Assistant Examiner—Maria Marvich
(74) Attorney, Agent, or Firm—Bereskin & Parr; Micheline Gravelle

(57) ABSTRACT

A peptide derived from apolipoprotein E termed apoEp1.B which includes amino acids 239–252 of the apolipoprotein E is described. The apoEp1.B peptide is a potent immune modulator that acts on a variety of immune cells. Interestingly, apoEp1.B is a dual modulator, capable of both inducing and suppressing an immune response. In particular, apoEp1.B has been shown to induce differentiation of stem cells into dendritic cells, to induce tumor cell differentiation and activation, to inhibit inflammation and to inhibit autoimmune disease.

55 Claims, 20 Drawing Sheets

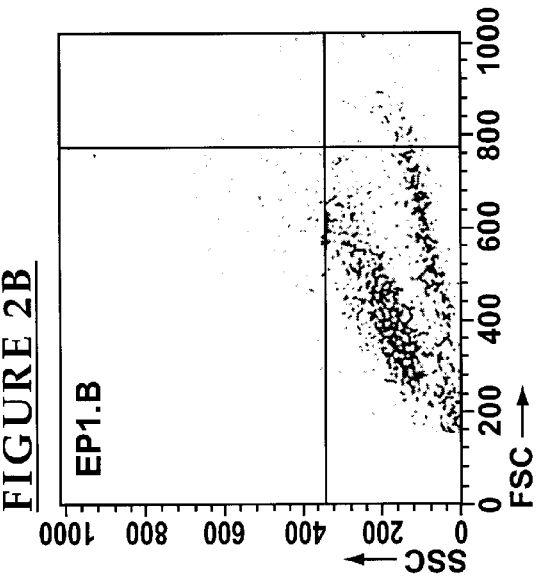
FIGURE 2A / FIGURE 2B
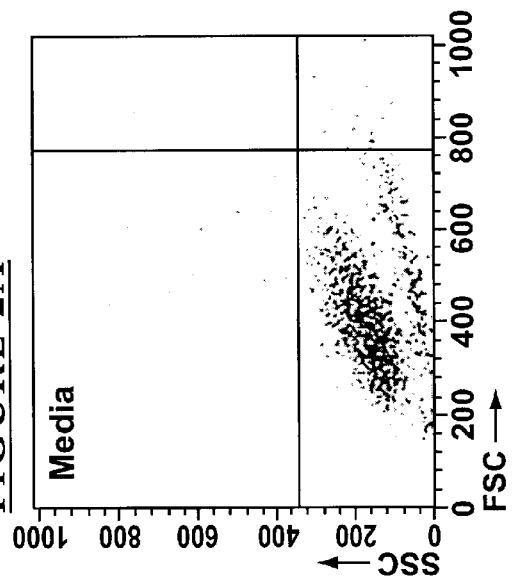
FIGURE 2C / FIGURE 2D

PEPTIDE, APOEP 1.B, COMPOSITIONS AND USES THEREOF

This application claim the benefit of provisional application Ser. No. 60/069,531 filed Dec. 12, 1997.

FIELD OF THE INVENTION

The invention relates to methods and compositions for immune modulation.

BACKGROUND OF THE INVENTION

The immune system is a complex, multifactorial defense system that protects the body from a wide range of infectious diseases including viruses, bacteria, parasites and fungi. Although critical for our survival, in certain instances, such as autoimmune disease, transplant rejection, allergies and inflammation, the immune system can be the cause of illness. In such instances it is desirable to suppress or tolerize the immune response.

The immune system is comprised of a large variety of cells derived from undifferentiated hematopoietic stem cells and includes phagocytes (such as neutrophil polymorphs, monocytes, macrophages and dendritic cells) and lymphocytes such as T cells and B cells and natural killer cells.

Dendritic cells are interesting immune cells as, depending on the circumstances, they can either activate or suppress an immune response. With regard to immune activation, dendritic cells (DCs) are potent lymphocyte stimulators and are extremely effective antigen presenting cells. Recently, considerable interest has been generated in the potential use of dendritic cells for the therapy of cancer and infectious diseases. DCs pulsed with tumour peptides elicit protective and antitumour immunity in mice (Mayordama et al., 1995). Patients with B cell lymphomas have been successfully vaccinated with autologous antigen-pulsed DC directly isolated from the blood (Hsu et al., 1996). Flt3 ligand, which induces DC maturation, resulted in tumour regression and antitumour immune response in mice (Lynch et al., 1997). Unfortunately, advances in treatment of tumors with DCs have been limited by their trace level in vivo. Efforts in this area are directed at increasing DC numbers and level of activation. With regard to tolerance, dendritic cells have recently been shown to be involved in the induction of central as well as peripheral tolerance and may be useful in treating autoimmunity, allergies and transplantation rejection.

SUMMARY OF THE INVENTION

The present inventors have prepared a peptide derived from apolipoprotein E termed apoEp1.B which includes amino acids 239–252 of the apolipoprotein E. The inventors have found that surprisingly, apoEp1.B is a potent immune modulator that acts on a variety of immune cells. Interestingly, apoEp1.B is a dual modulator, capable of both inducing and suppressing an immune response. In particular, apoEp1.B has been shown to induce differentiation of immature cells into dendritic cells, to induce tumor cell differentiation and activation, to inhibit inflammation and to inhibit autoimmune disease.

Accordingly, the present invention provides an isolated apoEp1.B peptide comprising amino acids 239–252 of an apolipoprotein E protein. In a preferred embodiment, the present invention provides an isolated apoEp1.B peptide having the amino acid sequence TQQIRLQAEIFQAR (SEQ.ID.NO.: 1) (murine) or AQQIRLQAEAFQAR (SEQ.ID.NO.: 2) (human). The invention also includes analogs, fragments, elongations and derivatives of a peptide of the invention. Analogs and derivatives of the peptides include peptides having the following sequences: TAQIRLQAEIFQAR (SEQ.ID.NO.: 3); TQAIRLQAEIFQAR (SEQ.ID.NO.: 4); TQQARLQAEIFQAR (SEQ.ID.NO.: 5) and TQQIALQAEIFQAR (SEQ.ID.NO.: 6). Fragments and elongations of the peptides include peptides that have the following sequences: QTQQIRLQAEIFQAR (SEQ.ID.NO.: 7) and QQIRLQAEIFQAR (SEQ.ID.NO.: 8). The present invention also provides a nucleic acid molecule encoding the apoEp1.B peptide, or an analog, fragment or derivative thereof.

The present invention further provides a method of immune modulation comprising administering an effective amount of an apoEp1.B peptide or a nucleic acid encoding an apoEp1.B peptide to a cell or animal in need thereof.

According to one embodiment, the peptide can induce immune tolerance. In particular, the present inventors have demonstrated that the apoEp1.B peptide can activate monocytes to differentiate into tolerogenic dendritic cells. The induction of tolerogenic dendritic cells can have a wide variety of therapeutic applications including inflammation, autoimmune disease and transplantation.

In another embodiment, the apoEp1.B peptide is useful in inhibiting inflammation. In a preferred embodiment, the peptide can inhibit atherosclerotic plaque formation in vivo.

In a further embodiment, the apoEp1.B peptide can be used to prevent or treat an autoimmune reaction or disease. The present inventors have also demonstrated that the apoEp1.B peptide can protect NOD mice from developing diabetes. In a preferred embodiment, the autoimmune disease is diabetes.

In a further aspect, the apoEp1.B peptide can be used to induce an immune response by activating immune cells. In one embodiment, the peptide, in combination with other cytokines such as IL-4, GM-CSF, TNFα and Flt3 ligand may induce immature dendritic cells to differentiate into mature immunogenic dendritic cells. Mature dendritic cells can be used in a wide variety of applications including tumor immunotherapy.

In another aspect, the apoEp1.B peptide can be used to treat tumors of immune origin by inducing their differentiation. In particular, the present inventors have demonstrated that the apoEp1.B peptide can induce the differentiation and activation of monocytic, monoblastic leukemia and lymphoma tumor cells.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which:

FIGS. 2(A–D) is a FACS analysis of J77A cells incubated with apoEp1.B (B and D) or with a control peptide (A and C) for 48 hours.

(B) untreated, surgery and (C) treated with apoEp1.B and surgery (arterial section shown).

Figure 11:
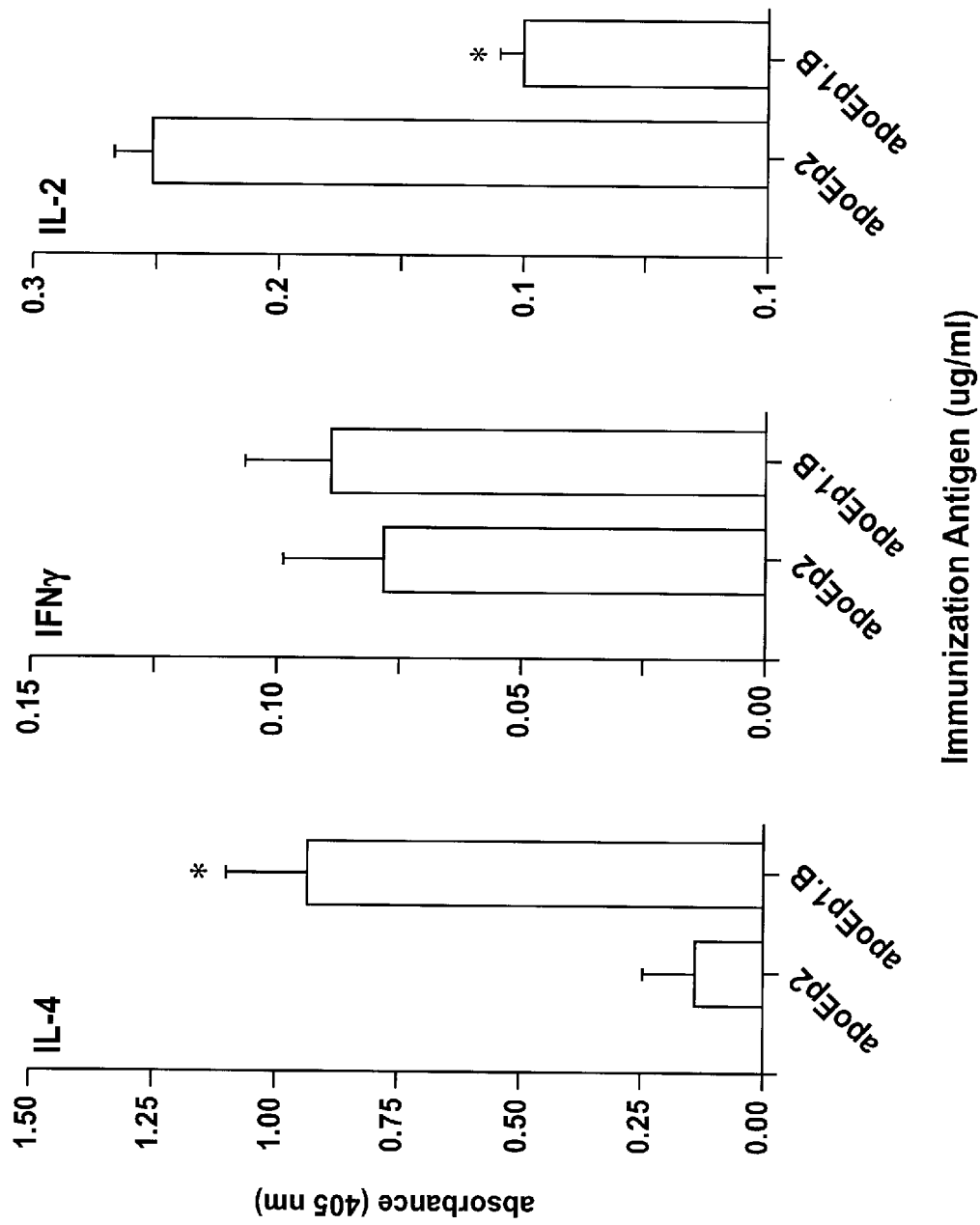

FIG. 11 shows histograms which illustrate the induction of Th2-like cells by apoEp1.B immunization.

Figure 12:
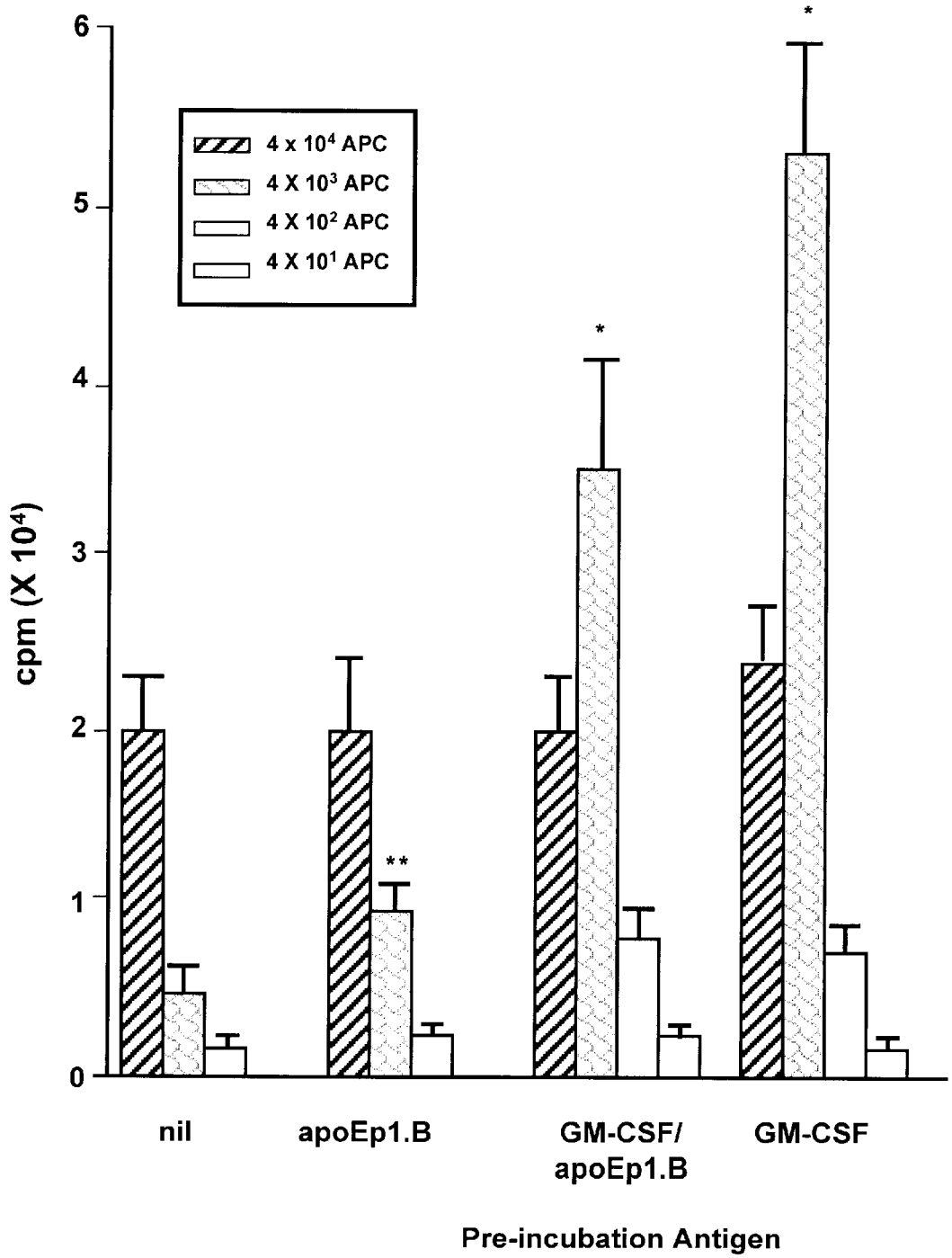

FIG. 12 shows a histogram which illustrates allostimulatory abilities of apoEp1.B treated cells.

Figure 13A:
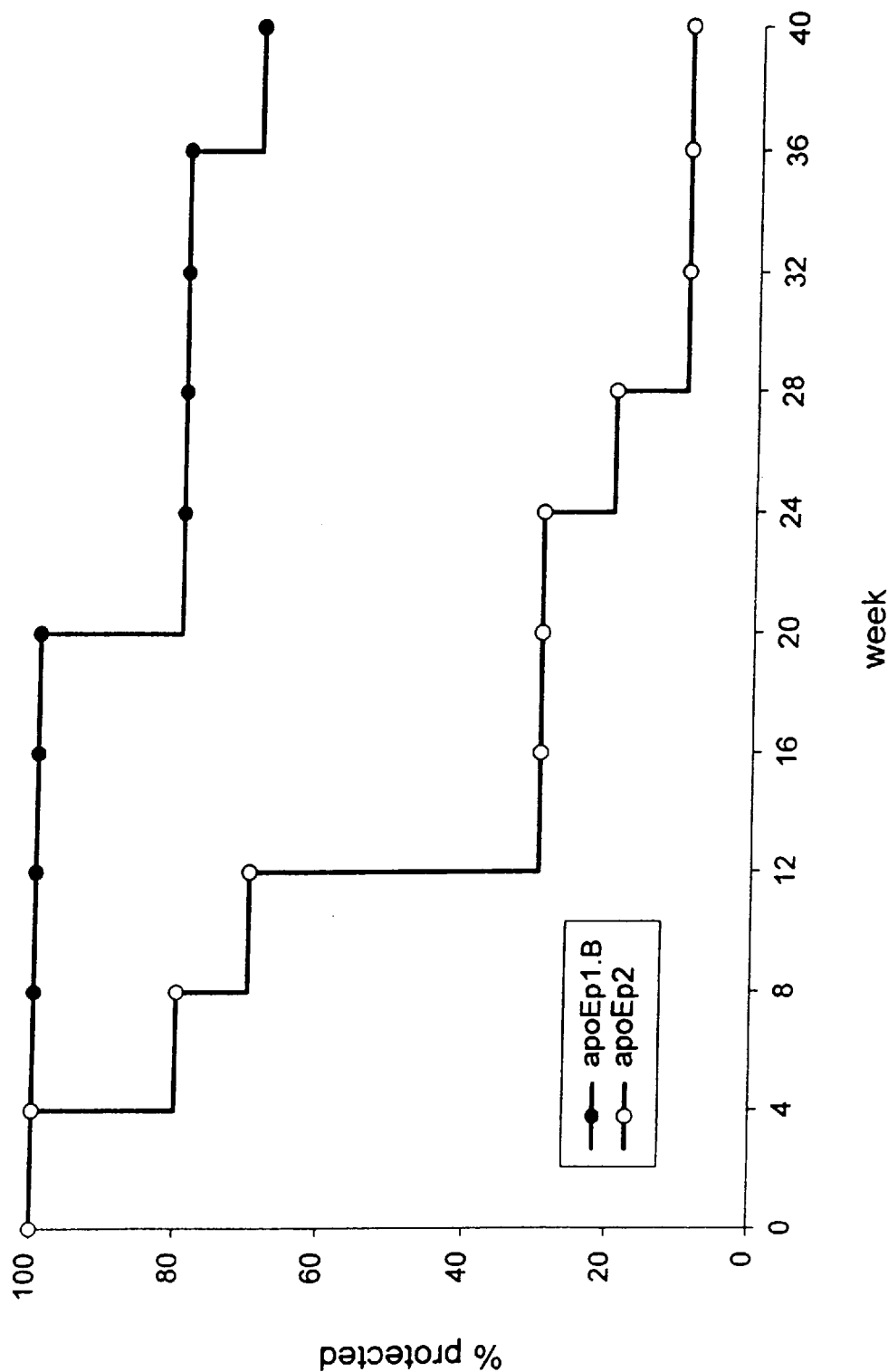

FIG. 13A is a graph which illustrates apoEp1.B protection of NOD mice from spontaneous diabetes.

Figure 13B:
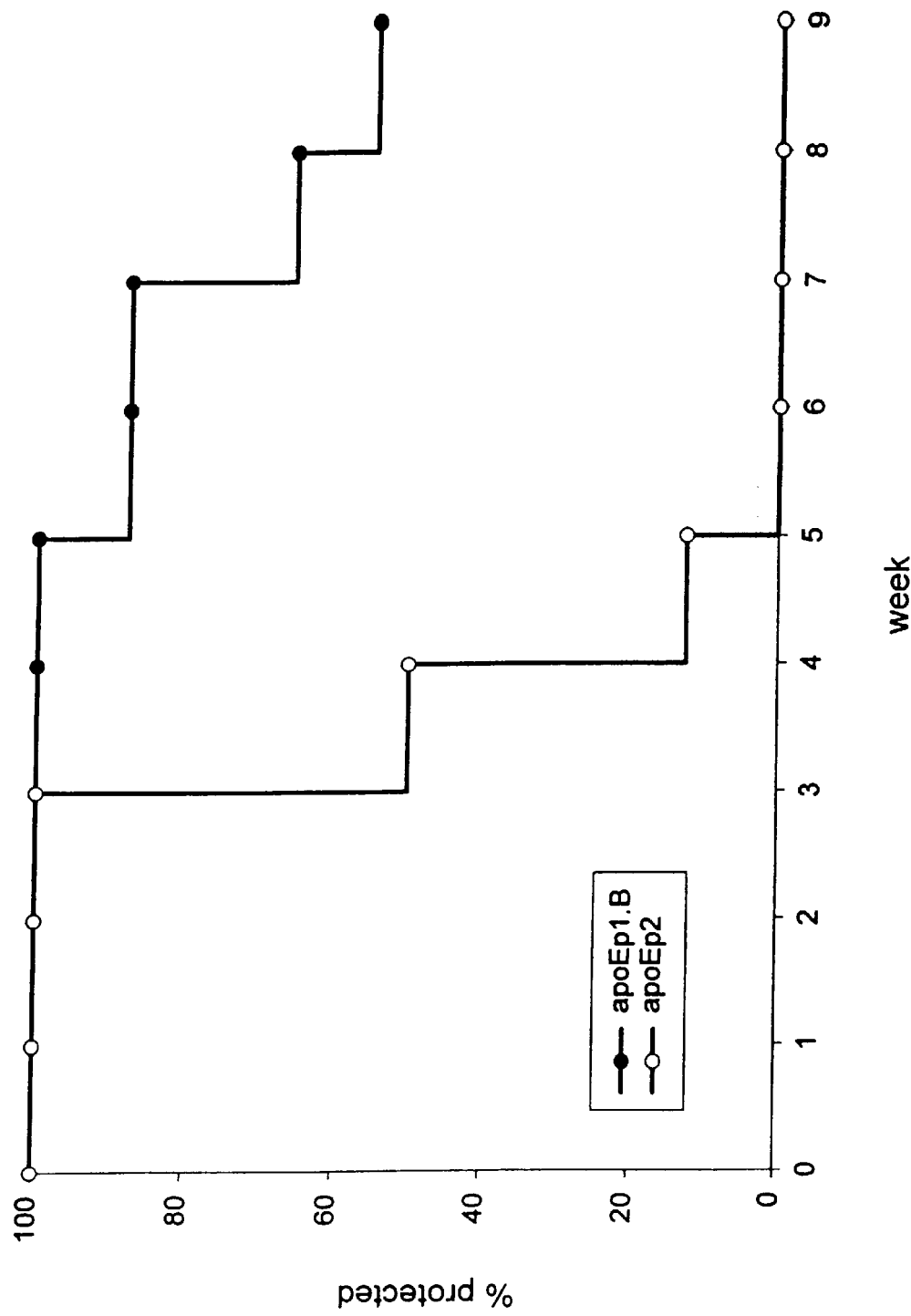

FIG. 13B is a graph which illustrate apoEp1.D protection of NOD mice from adoptively transferred diabetes.

Figure 14:
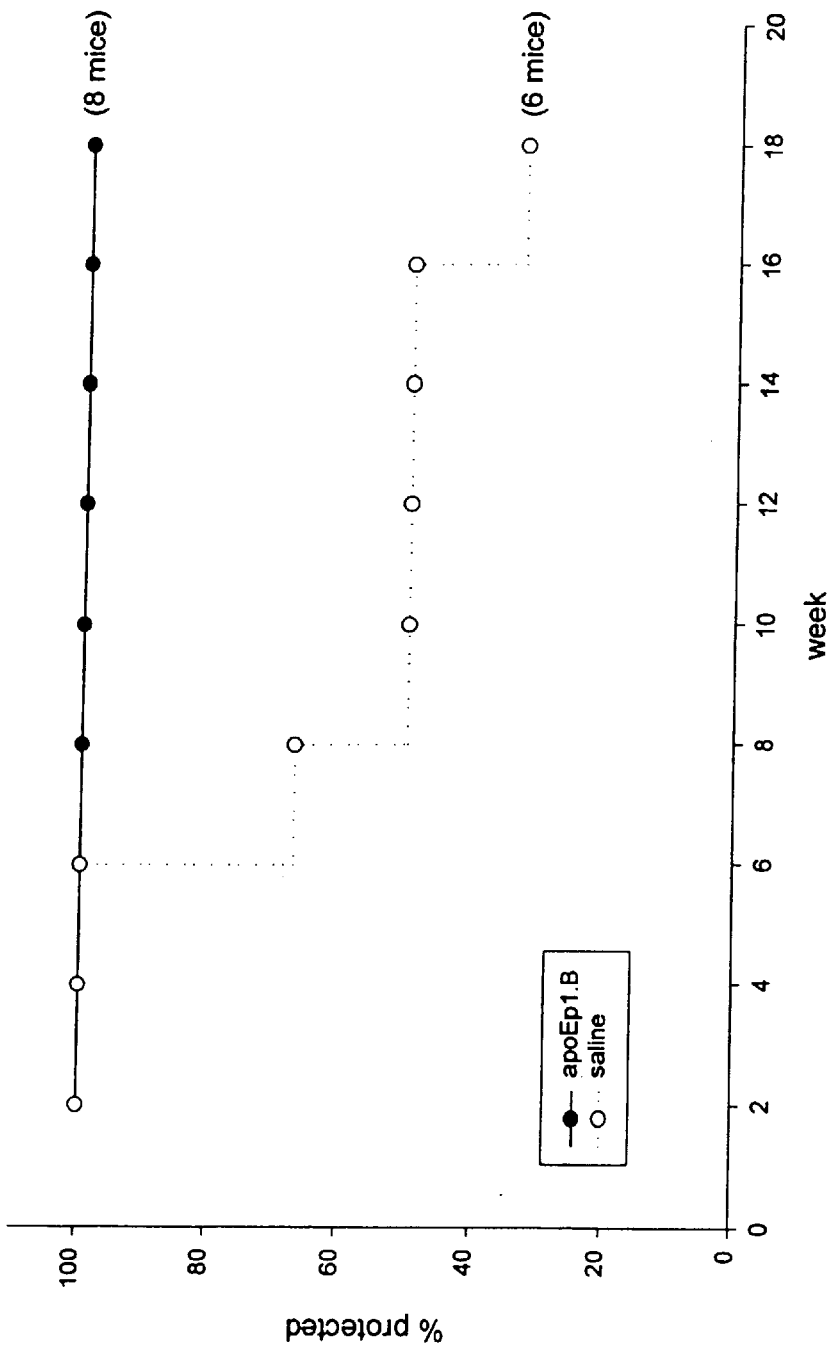
Figure 15A:
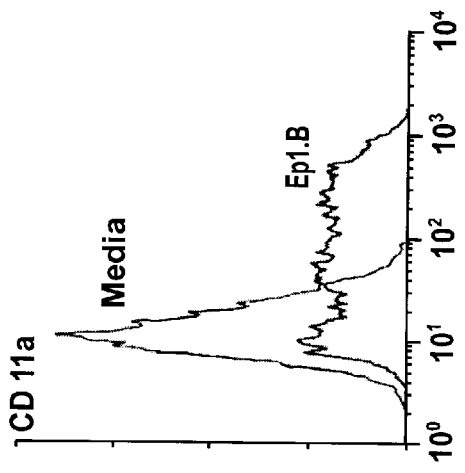
Figure 15B:
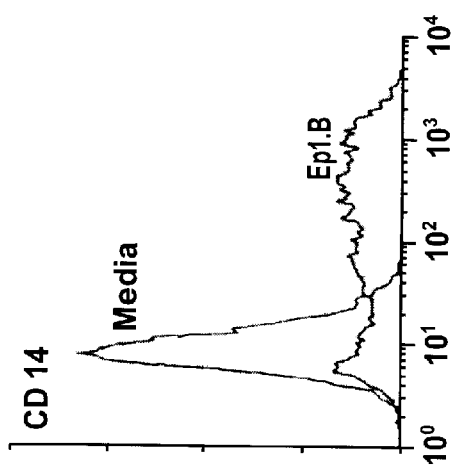
Figure 15C:
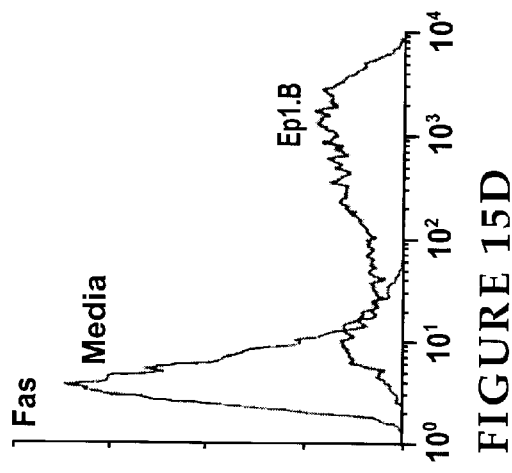
Figure 15D:
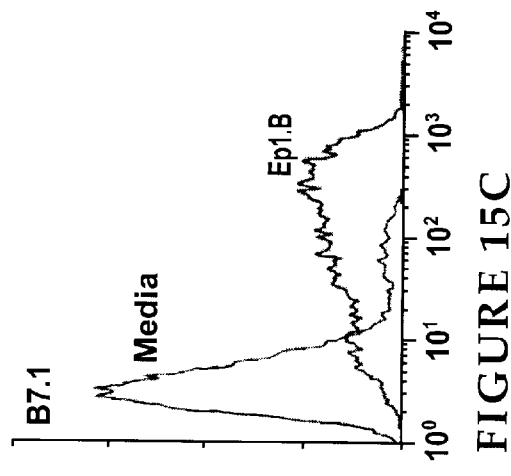

FIG. 14 is a graph showing the percentage of mice protected from diabetes versus time, in the presence and absence of apoEp1.B.

FIGS. 15A–D illustrate the effect of different concentrations of apoEp1.B on proliferation of U-937 cells.

Figure 16:
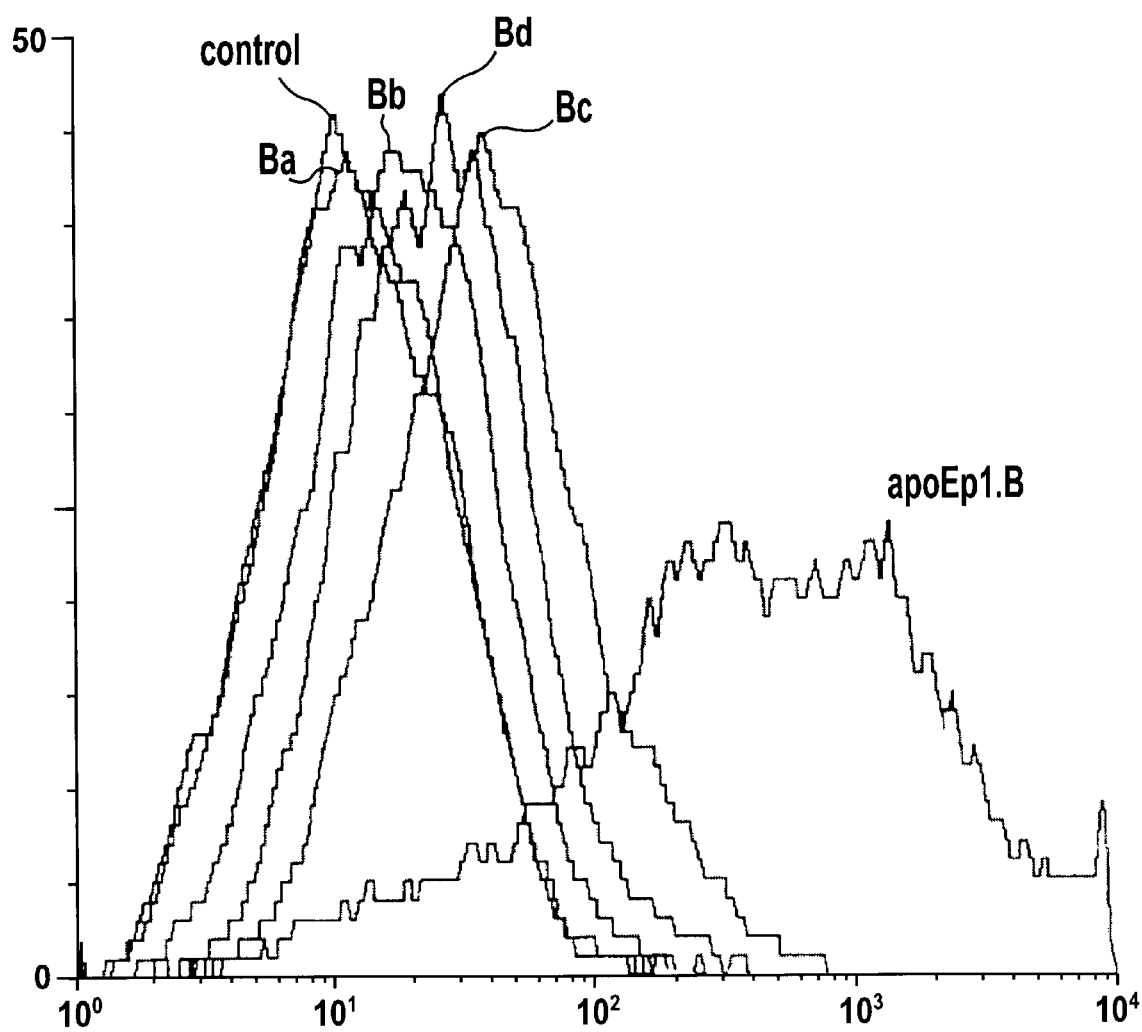

FIG. 16 shows a FACS analysis which illustrates that single amino acid deletions or elongations decrease the activity of apoEp1.B.

DETAILED DESCRIPTION OF THE INVENTION

As hereinbefore mentioned, the present inventors have prepared a peptide from both human and murine apolipoprotein E termed apoEp1.B (239–252) which is a potent immune modulator and can be used in a wide variety of applications.

I. PEPTIDES OF THE INVENTION

Broadly stated, the present invention provides an isolated apoEp1.B peptide comprising amino acids 239–252 of an apolipoprotein E protein or an analog, fragment, elongation or derivative thereof.

In one aspect, the present invention provides an isolated apoEp1.B peptide having the amino acid sequence TQQIRLQAEIFQAR (murine)(SEQ. ID. No. 1) or AQQIRLQAEAFQAR (human)(SEQ. ID. No. 2) or an analog, fragment, elongation or derivative of the peptide. The invention also includes a nucleic acid molecule encoding the apoEp1.B peptide, or an analog, fragment, elongation or derivative thereof.

The term "analog" includes any peptide having an amino acid residue sequence substantially identical to the human or mouse apoEp1.B sequence specifically shown herein in which one or more residues have been conservatively substituted with a functionally similar residue and which displays the ability to mimic apoEp1.B as described herein. Examples of conservative substitutions include the substitution of one non-polar (hydrophobic) residue such as alanine, isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another. The phrase "conservative substitution" also includes the use of a chemically derivatized residue in place of a non-derivatized residue provided that such polypeptide displays the requisite activity.

Analogs of the peptides include peptides having the following sequences: TAQIRLQAEIFQAR (SEQ.ID.NO.:3); TQAIRLQAEIFQAR (SEQ.ID.NO.:4); TQQARLQAEIFQAR (SEQ.ID.NO.:5) and TQQIALQAEIFQAR (SEQ.ID.NO.:6).

"Derivative" refers to a peptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Polypeptides of the present invention also include any polypeptide having one or more additions and/or deletions or residues relative to the sequence of a polypeptide whose sequence is shown herein, so long as the requisite activity is maintained.

The term "fragment" refers to any subject peptide having an amino acid residue sequence shorter than that of a peptide whose amino acid residue sequence is shown herein.

The term "elongation" refers to any subject peptide having an amino acid sequence longer by one or two amino acids (either at the carboxy or amino terminal end) than that of a peptide of the present invention. Preferably, the elongation occurs at the amino terminal end.

Fragments and elongations of the peptides include peptides that have the following sequences: QTQQIRLQAEIFQAR (SEQ.ID.NO.:7) and QQIRLQAEIFQAR (SEQ.ID.NO.:8).

The term "apoEp1.B peptide" or "peptide of the invention" as used herein includes a peptide comprising amino acid residues 239 to 252 of an apolipoprotein E protein and includes all analogs, fragments, elongations or derivatives of the apoEp1.B peptide including the sequences provided above in SEQ.ID.NOS.:1–8. Preferably, the apoEp1.B is the murine apoEp1.B sequence TQQIRLQAEIFQAR (SEQ. ID.

No. 1) or the human apoEp1.B sequence AQQIRLQAEAF-QAR (SEQ. ID. No. 2).

The apoEp1.B peptide may be modified to make it more therapeutically effective or suitable. For example, it may be cyclized as cyclization allows a peptide to assume a more favourable conformation. Cyclization of the apoEp1.B peptide may be achieved using techniques known in the art. In particular, disulphide bonds may be formed between two appropriately spaced components having free sulfhydryl groups. The bonds may be formed between side chains of amino acids, non-amino acid components or a combination of the two. In addition, the apoEp1.B peptide of the present invention may be converted into pharmaceutical salts by reacting with inorganic acids including hydrochloric acid, sulphuric acid, hydrobromic acid, phosphoric acid, etc., or organic acids including formic acid, acetic acid, propionic acid, glycolic acid, lactic acid, pyruvic acid, oxalic acid, succinic acid, malic acid, tartaric acid, citric acid, benzoic acid, salicylic acid, benzenesulphonic acid, and tolunesulphonic acids.

The apoEp1.B proteins of the invention may also be prepared by conventional techniques. For example, the peptides may be synthesized by chemical synthesis using techniques well known in the chemistry of proteins such as solid or solution phase synthesis (see for example J. M. Stewart, and J. D. Young, Solid Phase Peptide Synthesis, 2nd Ed., Pierce Chemical Co., Rockford Ill. (1984) and G. Barany and R. B. Merrifield, The Peptides: Analysis Synthesis, Biology editors E. Gross and J. Meienhofer Vol. 2 Academic Press, New York, 1980, pp. 3–254 for solid phase synthesis techniques; and M Bodansky, Principles of Peptide Synthesis, Springer-Verlag, Berlin 1984, and E. Gross and J. Meienhofer, Eds., The Peptides: Analysis, Synthesis, Biology, supra, Vol 1, for classical solution synthesis and Merrifield, 1964, J. Am. Chem. Assoc. 85:2149–2154) or synthesis in homogenous solution (Houbenweyl, 1987, Methods of Organic Chemistry, ed. E. Wansch, Vol. 15 1 and 11, Thieme, Stuttgart).

The apoEp1.B peptides of the invention may also be produced by recombinant DNA technology. To prepare the peptides of the invention by recombinant DNA techniques, a DNA sequence encoding the apoEp1.B peptide must be prepared. Consequently, the present invention also provides purified, and isolated nucleic acid having a nucleotide sequence encoding an apoEp1.B peptide comprising an amino acid sequence TQQIRLQAEIFQAR (SEQ. ID. No. 1) or an amino acid sequence AQQIRLQAEAFQAR (SEQ. ID. No. 2).

The present invention also provides an expression vector comprising a DNA molecule encoding an apoEp1.B peptide adapted for transfection or transformation of a host cell.

Accordingly, the nucleic acid molecules of the present invention may be incorporated in a known manner into an appropriate expression vector which ensures expression of the protein. Possible expression vectors include but are not limited to cosmids, plasmids, or modified viruses (e.g. replication defective retroviruses, adenoviruses and adeno-associated viruses). The vector should be compatible with the host cell used. The expression vectors are "suitable for transformation of a host cell", which means that the expression vectors contain a nucleic acid molecule of the invention and regulatory sequences selected on the basis of the host cells to be used for expression, which is operatively linked to the nucleic acid molecule. Operatively linked is intended to mean that the nucleic acid is linked to regulatory sequences in a manner which allows expression of the nucleic acid.

The invention therefore contemplates a recombinant expression vector of the invention containing a nucleic acid molecule of the invention, or a fragment thereof, and the necessary regulatory sequences for the transcription and translation of the inserted protein-sequence.

Suitable regulatory sequences may be derived from a variety of sources, including bacterial, fungal, viral, mammalian, or insect genes (For example, see the regulatory sequences described in Goeddel, Gene Expression Technology: Methods in Enzymology 185, Academic Press, San Diego, Calif. (1990). Selection of appropriate regulatory sequences is dependent on the host cell chosen as discussed below, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector.

The recombinant expression vectors of the invention may also contain a selectable marker gene which facilitates the selection of host cells transformed or transfected with a recombinant molecule of the invention. Examples of selectable marker genes are genes encoding a protein such as G418 and hygromycin which confer resistance to certain drugs, β-galactosidase, chloramphenicol acetyltransferase, firefly luciferase, or an immunoglobulin or portion thereof such as the Fc portion of an immunoglobulin preferably IgG.

Recombinant expression vectors can be introduced into host cells to produce a transformant host cell. The term "transformant host cell" is intended to include prokaryotic and eukaryotic cells which have been transformed or transfected with a recombinant expression vector of the invention. The terms "transformed with", "transfected with", "transformation" and "transfection" are intended to encompass introduction of nucleic acid (e.g. a vector) into a cell by one of many possible techniques known in the art. Prokaryotic cells can be transformed with nucleic acid by, for example, electroporation or calcium-chloride mediated transformation. Nucleic acid can be introduced into mammalian cells via conventional techniques such as calcium phosphate or calcium chloride co-precipitation, DEAE-dextran mediated transfection, lipofectin, electroporation or microinjection. Suitable methods for transforming and transfecting host cells can be found in Sambrook et al. (Molecular Cloning: A Laboratory Manual, 2nd Edition, Cold Spring Harbor Laboratory press (1989)), and other laboratory textbooks.

Suitable host cells include a wide variety of prokaryotic and eukaryotic host cells. For example, the proteins of the invention may be expressed in bacterial cells such as E. coli, insect cells (using baculovirus), yeast cells or mammalian cells. Yeast and fungi host cells suitable for carrying out the present invention include, but are not limited to Saccharomyces cerevisae, the genera Pichia or Kluyveromyces and various species of the genus Aspergillus. Mammalian cells suitable for carrying out the present invention include, among others: COS (e.g., ATCC No. CRL 1650 or 1651), BHK (e.g. ATCC No. CRL 6281), CHO (ATCC No. CCL 61), HeLa (e.g., ATCC No. CCL 2), 293 (ATCC No. 1573) and NS-1 cells. Other suitable host cells can be found in Goeddel, Gene Expression Technology: Methods in Enzymology 185, Academic Press, San Diego, Calif. (1991).

Another aspect of the invention provides a nucleotide sequence which hybridizes under high stringency conditions to a nucleic acid sequence which encodes an apoEp1.B peptide of the invention. Appropriate stringency conditions which promote DNA hybridization are known to those skilled in the art, or can be found in Current Protocols in Molecular Biology, John Wiley & Sons, N.Y. (1989), 6.3.1 6.3.6. For example, 6.0×sodium chloride/sodium citrate (SSC) at about 45° C., followed by a wash of 2.0×SSC at 50° C. may be employed. The stringency may be selected based on the conditions used in the wash step. By way of example, the salt concentration in the wash step can be selected from a high stringency of about 0.2×SSC at 50° C. In addition, the temperature in the wash step can be at high stringency conditions, at about 65° C.

II. UTILITY OF THE PEPTIDES

A. Therapeutic Methods

The inventors have surprisingly found that the apoEp1.B peptide of the invention is a potent immune modulator that acts on a variety of immune cells. Interestingly, apoEp1.B is a dual modulator, capable of both inducing and suppressing an immune response. As mentioned previously, the apoEp1.B peptide comprises amino acids 239–252 of full length apolipoprotein E (apoE) including fragments, elongations, analogs and derivatives of the peptide. The inventors have shown that apoEp1.B but not apoE or a peptide comprising amino acids 237–250 of apoE can induce the activation and differentiation of immune cells.

Accordingly, the present invention provides a method of immune modulation comprising administering an effective amount of an apoEp1.B peptide or a nucleic acid encoding an apoEp1.B peptide to a cell or animal in need thereof.

The apoEp1.B peptide can be used to induce immune tolerance. In particular, the present inventors have demonstrated that the apoEp1.B peptide can activate immature cells to differentiate into tolerogenic dendritic cells. Accordingly, the present invention provides a method of inducing immune tolerance comprising administering an effective amount of an apoEp1.B peptide or a nucleic acid encoding an apoEp1.B peptide to a cell or animal in need thereof. The induction of tolerogenic dendritic cells can have a wide variety of therapeutic applications including inflammation, autoimmune disease and transplantation. The tolerogenic dendritic cells can be induced in vitro and then transferred to a recipient requiring the cells. Alternatively, the tolerogenic cells may be directly induced in vivo.

The inventors have shown that the apoEp1.B peptide is useful in inhibiting inflammation. Accordingly, the present invention provides a method for inhibiting inflammation comprising administering an effective amount of an apoEp1.B peptide or a nucleic acid encoding an apoEp1.B peptide to a cell or an animal in need thereof. In a preferred embodiment, the peptide can inhibit athersclerotic plaque formation in vivo. Other inflammatory diseases that may be treated using the apoEp1.B peptide or nucleic acid encoding the apoEp1.B peptide include, arthritis, inflammatory bowel disease (IBD), Sjogren's syndrome, atherosclerosis, restenosis, transplant rejection, transplant vasculopathy, asthma, acute respiratory distress syndrome, allergy, psoriasis, multiple sclerosis, systemic lupus, acute glomerulonephrihs, spinal cord trauma, and others.

In a further embodiment, the apoEp1.B peptide can be used to prevent an autoimmune reaction or disease. The present inventors have demonstrated that the apoEp1.B peptide can protect NOD mice from developing diabetes. Accordingly, the present invention provides a method for treating or preventing an autoimmune disease comprising administering an effective amount of an apoEp1.B peptide or a nucleic acid encoding an apoEp1.B peptide to an animal in need thereof. In a preferred embodiment, the autoimmune disease is diabetes. Other autoimmune diseases which may be treated using the apoEp1.B peptide or nucleic acid encoding the apoEp1.B peptide include multiple sclerosis, EAE which is the mouse model of multiple sclerosis, rheumatoid arthritis, Sjogren's syndrome, lupus (SLE), autoimmune thyroid disease and others.

In a further aspect, the apoEp1.B peptide can be used to induce an immune response by activating immune cells. Accordingly, the present invention provides a method of inducing an immune response comprising administering an effective amount of an apoEp1.B peptide or a nucleic acid encoding an apoEp1.B peptide to an animal in need thereof. In one embodiment, the peptide, in combination with other cytokines such as IL-4, GM-CSF, TNFα and Flt3 ligand induce immature dendritic cells to differentiate into mature immunogenic dendritic cells. Mature dendritic cells can be used in a wide variety of applications including tumor immunotherapy.

In another aspect, the apoEp1.B peptide can be used to treat tumors of immune origin by inducing their differentiation. In particular, the present inventors have demonstrated that the apoEp1.B peptide can induce the differentiation and activation of monocytic, monoblastic leukemia and lymphoma tumor cells. Accordingly, the present invention provides a method of treating a tumor comprising administering an effective amount of an apoEp1.B peptide or a nucleic acid encoding an apoEp1.B peptide to an animal in need thereof.

The apoEp1.B peptide or nucleic acid encoding the apoEp1.B peptide may also be used to treat or prevent other diseases or conditions requiring immune activation (including infectious diseases such as viral infections) and immune tolerance (including tissue or organ transplantation, allergies and the above noted inflammatory and autoimmune diseases).

Administration of an "effective amount" of the apoEp1.B peptide or nucleic acid of the present invention is defined as an amount effective, at dosages and for periods of time necessary to achieve the desired result. The effective amount of a compound of the invention may vary according to factors such as the disease state, age, sex, and weight of the animal. Dosage regima may be adjusted to provide the optimum therapeutic response. For example, several divided doses may be administered daily or the dose may be proportionally reduced as indicated by the exigencies of the therapeutic situation. The term "animal" as used herein includes all members of the animal kingdom including humans.

In all of the above described therapeutic methods, the apoEp1.B peptide may be administered in vivo or ex vivo. In ex vivo applications, the apoEp1.B peptide may be administered to cells that have been removed from the patient in an in vitro culture. After incubating the cells and peptide for a period of time sufficient for the desired effect, the cells may be re-introduced into the patient's body. In one example, monocytes may be removed from a patient and cultured with apoEp1.B to allow them to mature. In addition, tumor antigens or autoantigens may be added when treating cancer or autoimmune diseases, respectively. The mature monocytes expressing antigen can be re-introduced into the patient and will induce an immune response to the tumor or autoantigen.

B. Pharmaceutical Compositions

The present invention includes pharmaceutical compositions containing the apoEp1.B peptide or nucleic acid or substances which modulate the effects of apoEp1.B for use in the described methods for modulating the immune response.

Such pharmaceutical compositions can be for intralesional, intravenous, topical, rectal, parenteral, local, inhalant or subcutaneous, intradermal, intramuscular, intrathecal, transperitoneal, oral, and intracerebral use. The composition can be in liquid, solid or semisolid form, for example pills, tablets, creams, gelatin capsules, capsules, suppositories, soft gelatin capsules, gels, membranes, tubelets, solutions or suspensions. The apoEp1.B peptide is preferably injected in a saline solution either intravenously, intraperitoneally or subcutaneously.

Several modes of administration are available when using a composition containing a nucleic acid molecule encoding an apoEp1.B protein. Recombinant molecules comprising an nucleic acid sequence encoding an apoEp1.B protein, or fragment thereof, may be directly introduced into cells or tissues in vivo using delivery vehicles such as retroviral vectors, adenoviral vectors and DNA virus vectors. They may also be introduced into cells in vivo or in vitro using physical techniques such as microinjection and electroporation or chemical methods such as coprecipitation and incorporation of DNA into liposomes. Recombinant molecules may also be delivered in the form of an aerosol or by lavage. The nucleic acid molecules of the invention may also be applied extracellularly such as by direct injection into cells.

The pharmaceutical compositions of the invention can be intended for administration to humans or animals. Dosages to be administered depend on individual needs, on the desired effect and on the chosen route of administration.

The pharmaceutical compositions can be prepared by per se known methods for the preparation of pharmaceutically acceptable compositions which can be administered to patients, and such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985).

On this basis, the pharmaceutical compositions include, albeit not exclusively, the active compound or substance in association with one or more pharmaceutically acceptable vehicles or diluents, and contained in buffered solutions with a suitable pH and iso-osmotic with the physiological fluids. The pharmaceutical compositions may additionally contain other agents to enhance the efficacy of the apoEp1.B peptide or nucleic acid.

C. Peptide Mimetics

The present invention also include peptide mimetics of the apoEp1.B peptides of the invention. For example, a peptide derived from a binding domain of apoEp1.B will interact directly or indirectly with an associated molecule in such a way as to mimic the native binding domain. Such peptides may include competitive inhibitors, enhancers, peptide mimetics, and the like. All of these peptides as well as molecules substantially homologous, complementary or otherwise functionally or structurally equivalent to these peptides may be used for purposes of the present invention.

"Peptide mimetics" are structures which serve as substitutes for peptides in interactions between molecules (See Morgan et al (1989), Ann. Reports Med. Chem. 24:243–252 for a review). Peptide mimetics include synthetic structures which may or may not contain amino acids and/or peptide bonds but retain the structural and functional features of a peptide, or enhancer or inhibitor of the invention. Peptide mimetics also include peptoids, oligopeptoids (Simon et al (1972) Proc. Natl. Acad, Sci USA 89:9367); and peptide libraries containing peptides of a designed length representing all possible sequences of amino acids corresponding to a peptide of the invention. Peptide mimetics may be designed based on information obtained by systematic replacement of L-amino acids by D-amino acids, replacement of side chains with groups having different electronic properties, and by systematic replacement of peptide bonds with amide bond replacements. Local conformational constraints can also be introduced to determine conformational requirements for activity of a candidate peptide mimetic. The mimetics may include isosteric amide bonds, or D-amino acids to stabilize or promote reverse turn conformations and to help stabilize the molecule. Cyclic amino acid analogues may be used to constrain amino acid residues to particular conformational states. The mimetics can also include mimics of inhibitor peptide secondary structures. These structures can model the 3-dimensional orientation of amino acid residues into the known secondary conformations of proteins. Peptoids may also be used which are oligomers of N-substituted amino acids and can be used as motifs for the generation of chemically diverse libraries of novel molecules.

Peptides of the invention may also be used to identify lead compounds for drug development. The structure of the peptides described herein can be readily determined by a number of methods such as NMR and X-ray crystallography. A comparison of the structures of peptides similar in sequence, but differing in the biological activities they elicit in target molecules can provide information about the structure-activity relationship of the target. Information obtained from the examination of structure-activity relationships can be used to design either modified peptides, or other small molecules or lead compounds which can be tested for predicted properties as related to the target molecule. The activity of the lead compounds can be evaluated using assays similar to those described herein.

Information about structure-activity relationships may also be obtained from co-crystallization studies. In these studies, a peptide with a desired activity is crystallized in association with a target molecule, and the X-ray structure of the complex is determined. The structure can then be compared to the structure of the target molecule in its native state, and information from such a comparison may be used to design compounds expected to possess desired activities.

The following non-limiting examples are illustrative of the present invention:

EXAMPLES

Example 1

ApoEp1.B Induces Dendritic Cells and Differentiation of Tumor Cells

Materials and Methods

Reagents

Phorbol, 12-myristate, 13-acetate (PMA) (Calbiochem, La Jolla, Calif.) was dissolved in ethanol and stored at −80° C.

Mice

C57BL/6J(B6) (H2b), apoE knockout (H2b), and BALB/c (H2d) mice between 8 to 18 weeks used in this study were purchased from Jackson Laboratories, Bar Harbor, Me. Mice were fed a regular mouse chow (#5012), low in fat (4.5% wt/wt) and cholesterol (0.022% wt/wt) (Ralston, Purina, St. Louis, Mo.).

Cells and Culture Medium

Murine monocytic PU5-1.8 and J77A1.4 transformed cell lines, human monoblastic leukemia THP-1 and U-937, and murine B cell lymphoma A20 cells were cultured in RPMI 1640 medium (Gibco Laboratories, Grand Island, N.Y.) containing 5×105 M 2ME, 10 mM HEPES, 2 mM glutamine, 5.0 IU/ml penicillin streptomycin (Gibco) and 10%. heat inactivated Fetal Bovine Serum (FBS) (Hyclone Laboratories Inc., Logan, Utah)(cRPMI).

Peptide Synthesis and Purification and Proteins

Peptides were synthesized on a Beckman 990C peptide synthesizer as previously described (MacNeil et al., 1993). Peptides were then purified by HPLC on a reverse phase C18 column with wateracetonitrile gradient. Peptides were dissolved at 2 mg/ml in distilled $H_2O$ and filter sterilized through a 0.22 $\mu$m filter and further diluted in either cRPMI 1640 before use in proliferation assays, or emulsified in CFA or IFA for immunization of mice. Human plasma VLDL purified apoE (Calbiochem) was used as native apoE.

Single Cell Suspension Preparation

Mice were euthanized in a $CO_2$ chamber and either spleens or lymph nodes were removed aseptically and immersed in ice-cold PBS. Cells were separated by mincing tissues through a fine-mesh sieve. The cells were then pelleted by centrifugation at 1500 rpm for 5 min and supernatant discarded. Erythrocytes in spleen preparations were lysed using ACK lysis buffer (0.15M $NH_4Cl$, 1.0 mM $KHCO_3$, 0.1 mM $Na_2EDTA$, pH 7.3) for 2 minutes at room temperature and then resuspended in PBS and pelleted again twice to wash cells.

T Cell Proliferation Assay

BALB/c mice were injected under light anesthesia with 50 $\mu$l volumes containing 0, 1, 10 or 100 $\mu$g/ml of apoE peptide emulsified in IFA or CFA in the hind footpad. After 10 days draining (popliteal) lymph nodes were removed and T cells were purified by passage through nylon wool. $5 \times 10^5$ purified T cells and $2 \times 10^5$ gamma-irradiated ($^{60}Co$, 2500 rads)(Atomic Energy, Canada) autologous spleen APC's were incubated with 0, 1, 10, or 100 $\mu$g/ml apoE peptide in 96 well flat bottom microtitre plates at 5% $CO_2$, 37° C. for 3 days. PPD (20 $\mu$g/ml) served as a positive control where CFA was used. Either APC's or T cells alone incubated with either stimulating peptide served as negative controls. 50 $\mu$l [$^3$H]-TdR (0.5 $\mu$Ci/well) was added for an additional 18 hours and then cells were then harvested (Tomtec, Orange, Conn.). [$^3$H]-TdR incorporation was measured on a Microbeta Liquid Scintillation Counter (Wallac, Turku, Finland).

Proliferation Assays

Unprimed spleen or peritoneal exudate cells (PEC's) were incubated with 0, 1, 10, or 100 $\mu$g/ml apoEp1.B or negative control in 96 well flat bottom microtitre plates at 5% $CO_2$, 37° C. for 2 days. 50 $\mu$l [$^3$H]-TdR (0.5 $\mu$Ci/well) was added for an additional 18 hours and then cells were then harvested (Tomtec, Orange, Conn.). [$^3$H]-TdR incorporation was measured on a Microbeta Liquid Scintillation Counter (Wallac, Turku, Finland). PU5-1.8, J77A1.4, A20, and U-937 cell lines were treated similarly, but incubated with peptide for 12 hours prior to addition of [$^3$H]-TdR for an additional 18 hours. Results from U-937 cell lines are presented in FIG. 15. Cell supernatants were harvested from most cell cultures before radioisotype addition and assayed for cytokine content.

Mixed Leukocyte Reaction Assays

Primary allogeneic MLR was set up with NOD splenocytes as stimulators and nylon wool enriched BALB/c naive T cells as responders. Stimulator cells were pre-incubated for 3 days with different combinations of apoEp1.B, GM-CSF, and PU5-1.8 supernatant containing TNF. Stimulator cells were then treated with mitomycin C (50 $\mu$g/ml, 20 min at 37° C.; Sigma) and co-cultured with $4 \times 10^4$ responder for 3 days at which time cells were pulsed with 50 $\mu$l [$^3$H]-TdR (0.5 $\mu$Ci/well) for 24 hr. Cells were harvested (Tomtec) and [$^3$H]-TdR incorporation was measured on a Microbeta Liquid Scintillation Counter (Wallac). Each bar represents the mean cpm from triplicate cultures.

Cytokine Analysis

Culture supernatants were tested for IL-2, IL-4 and $IFN_\gamma$ concentration using sandwick ELISA assays. Manufacturer's (Pharmingen) protocols were followed. 96-well microtitre ELISA plates were coated with 50 $\mu$l, 1 $\mu$g/ml $\alpha$-IL-2, $\alpha$-IL-4 or $\alpha$-$IFN_\gamma$ mAB in coating buffer (0.1 M $NaHCO_3$, pH 8.2) overnight at 4° C. Plates were washed twice with PBS-T (PBS, Tween-20 (Sigma, St. Louis, Mo.) and plates were blocked for 2 hr at room temperature with 100 $\mu$l blocking buffer (PBS, 5% BSA). Plates were washed twice and 50 $\mu$l samples were added in triplicate for an overnight, 4° C. incubation. Plates were then washed 5 times and following a 2 hr room temperature incubation period with 50 $\mu$l, 1 $\mu$g/ml biotinylated $\alpha$-IL-2, $\alpha$-IL-4 or $\alpha$-IFN$\gamma$ mAB (Pharmingen), plates were washed 8 times. 50 $\mu$l, 1 $\mu$g/ml streptavidin-alkaline phosphatase (Pharmingen) was then added for 1 hr at room temperature. Following 8 washes, 50 $\mu$l p-nitrophenyl phosphate substrate (pNPP (Sigma)) was added and absorbance determined at O.D. 405 nm using a microplate reader (Biorad, Hercules, Calif.) after colour had developed.

Immunofluorescence and Flow Cytometry $1 \times 10^6$ cells were washed with ice cold PBS and resuspended in 25 $\mu$l PBS and incubated with 10 $\mu$l normal mouse serum and fluorochrome conjugated anti-mouse D11a, CD11b, CD14, MHC class II, CD95, CD62L, CD62E, B7-1, B7-2 and ICAM-1 Pharmingen, Mississauga, Canada) monoclonal antibodies (mAb's) for 45 minutes on ice. endritic cell markers DEC-205, 33D1, CD11c (N418) unconjugated antibodies were imilarly treated, however, following primary antibody incubation,cells were washed 3 times and a secondary goat anti-rat (for 33D1 and DEC-205 ab's) and goat anti-hamster (for CD11c ab) fluorochrome-conjugated antibody was then added for 45 min on ice. Cells were then washed three times. All samples were resuspended in 300 $\mu$l PBS and the fluorescence of stained cells was analyzed on a FACScan flow cytometer (Becton Dickinson, Mountain View, Calif.) and data collected was analyzed using Lysis II (Becton-Dickinson) software.

Cell Cycle Analysis $1 \times 10^6$ cells were washed and resuspended in hypotonic propidium iodide (PI) staining solution (0.1% [w/v] sodium citrate, 0.1[v/v] Triton X-100, 0.05 $\mu$g/ml propidium iodide) and left to stain in the dark overnight at 4° C. Cells were analyzed on a FACScan flow cytometer and the percentage of cells in each phase of the cell cycle were quantitated using ModFit software (Becton Dickinson). Aggregates were excluded from the analysis with the use of the doublet discrimination module and subsequent gating on the linear red (FL2) fluorescence area and width parameters.

Intraperitoneal Injection

BALB/c mice were injected i.p. with 300 µg apoE peptide and 48 hours later PECs were collected post-mortem by peritoneal lavage using ice cold saline.

Adoptive Transfer Studies

RBC-depleted diabetogenic splenocytes from 17–20 wk-old female NOD mice were resuspended in saline. 8 to 10 wk old NOD.SCID mice were injected i.p. with 0.2 µl saline containing $10^7$ of the diabetogenic splenocytes. These same mice were then immunized with either 200 µg/ml apoEp1.B or 200 µg/ml apoEp2 via the footpad. Urine glucose levels were monitored biweekly using glucose enzymatic test strips (Eli Lilly, Toronto, Ont.). Once urine tested positive, then blood glucose levels (BGL) were tested using Glucometer Encore (Miles/Bayer). Mice exhibiting BGL >11.1 mmol/L (200 mg/dl) for 2 consecutive weeks were considered diabetic.

RESULTS

ApoEp1.B Peptide Induces Dendritic-like Cell Morphology

Unprimed splenocytes, enriched spleen monocytes and monocytic PU5-1.8 and J77A4.1 cell lines from BALB/c mice were incubated with 0, 1, 10, or 100 µg/ml apoEp1.B (239–252) or negative control apoEp1.D (236–249) peptide to assess activity. After only 2 hr, apoEp1.B, but not apEp1.D-incubated cells started to detach from plastic plates and aggregate in suspension optimally at 100 µg/ml. After 24 hr, morphologically these cells appeared less rounded, more granular. Photographs were taken after 24 hours, the results are shown in FIG. 1 (magnification 400×). At 48 hours they displayed dendritic-like processes. FACS analysis confirmed an increase in cell size and granularity (FIG. 2).

ApoEp1.B Peptide Induces DC-like Marker Expression

Figure 1A:
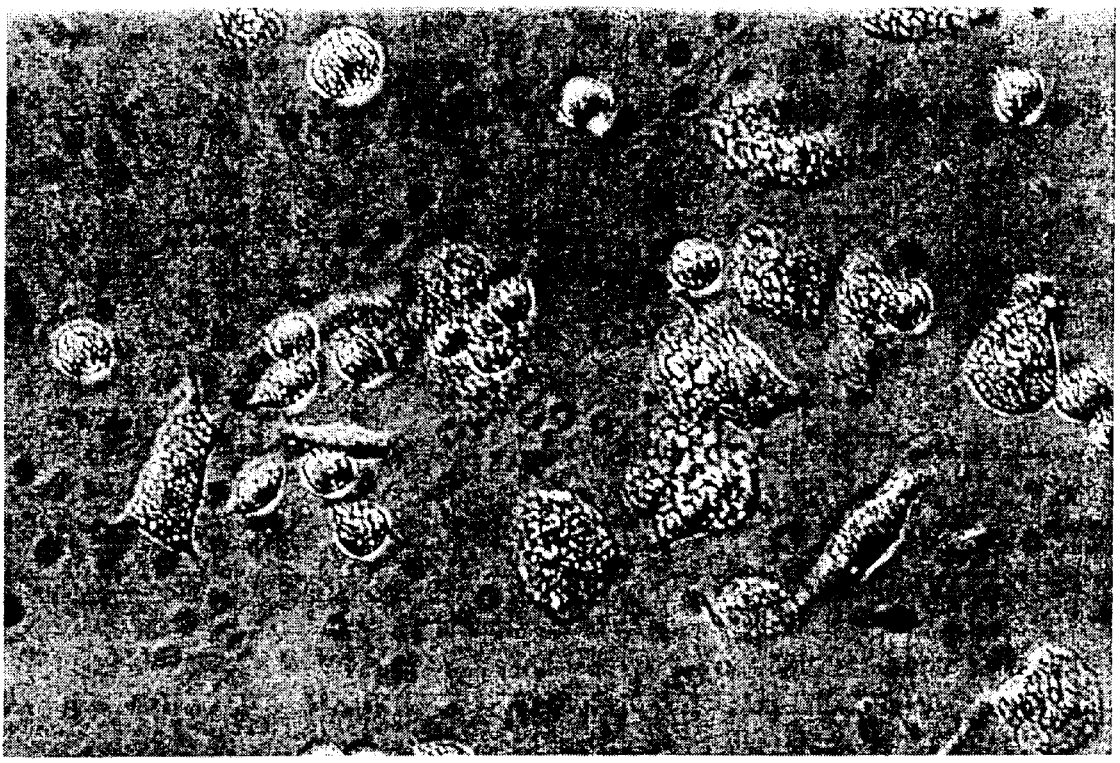
FIGS. 1A and B are photographs of spleen cells incubated with apoEp1.B (B) or a control peptide (A) for 48 hours.
Figure 1B:
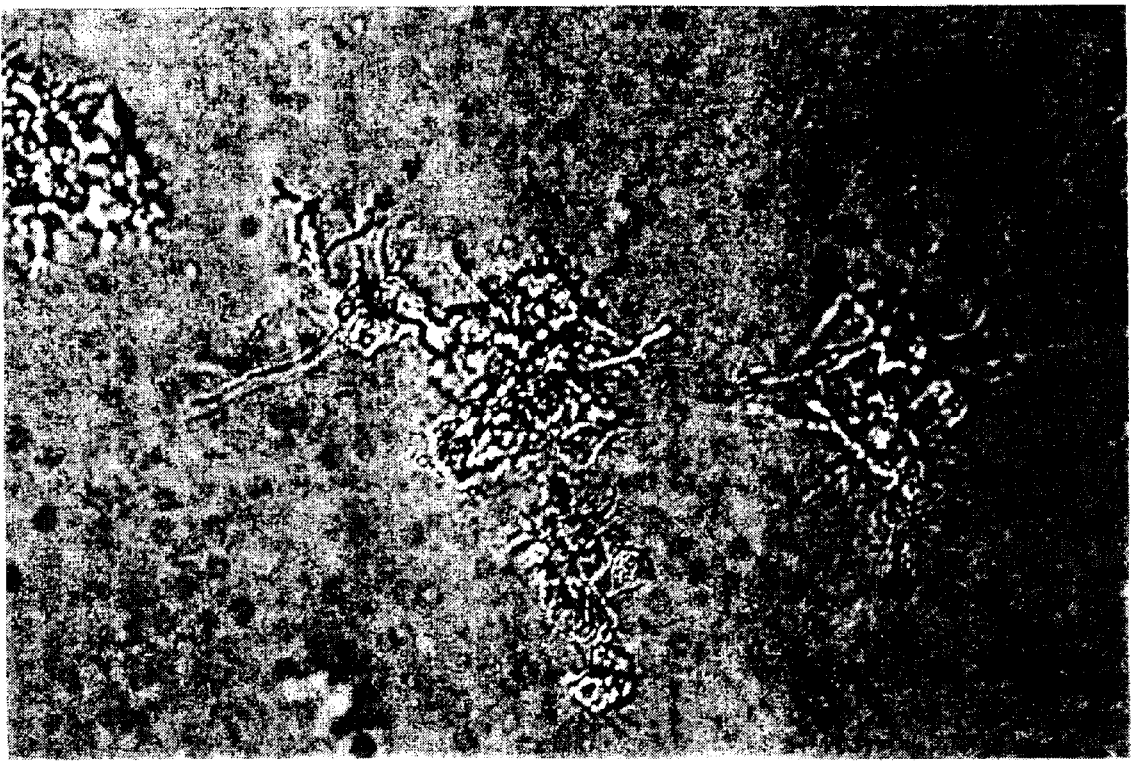
FIGS. 1C and D are photographs of PU5-1.8 cells incubated with apoEp1.B (D) or a control peptide (C) for 48 hours.
Figure 1C:
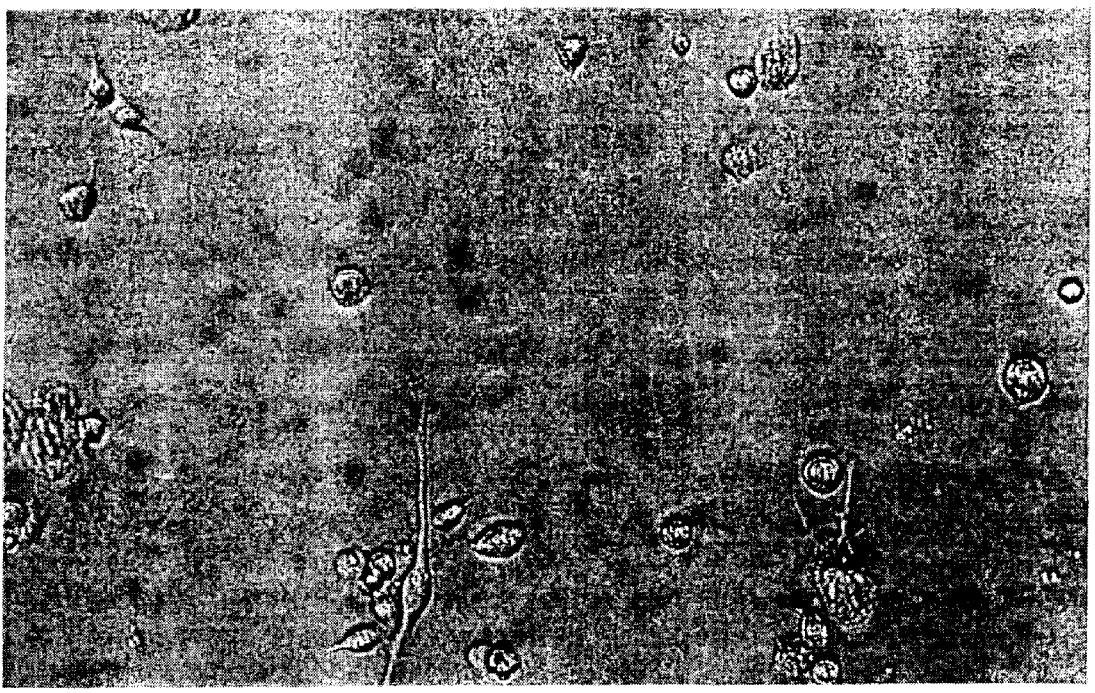
Figure 1D:
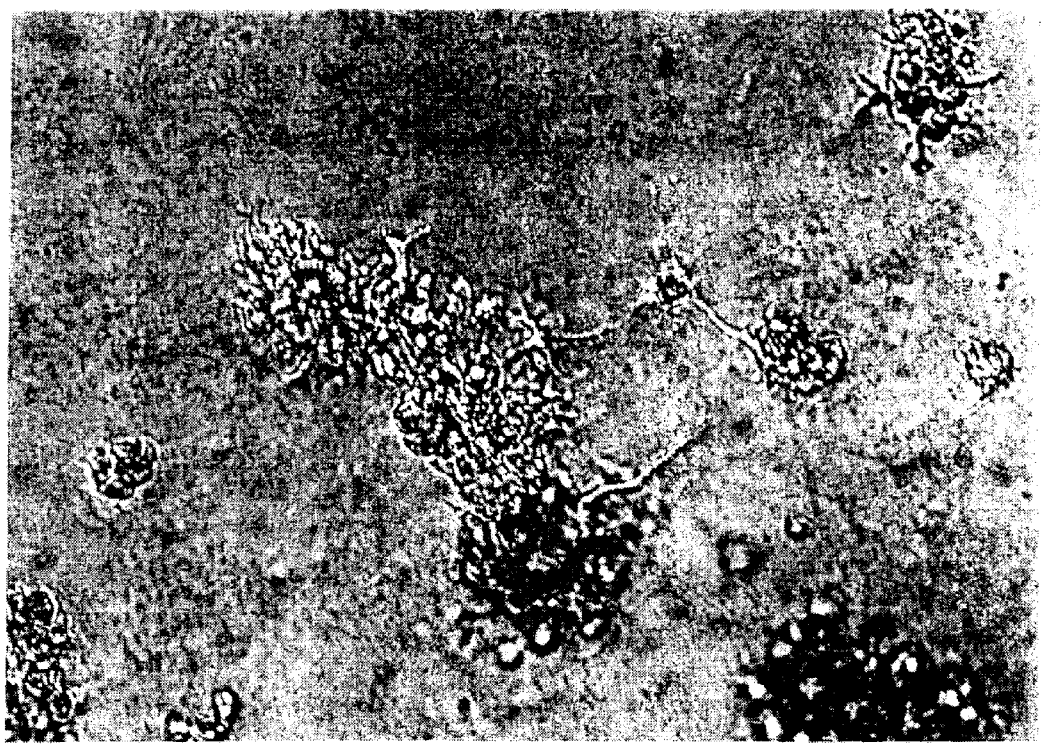
Figure 3:
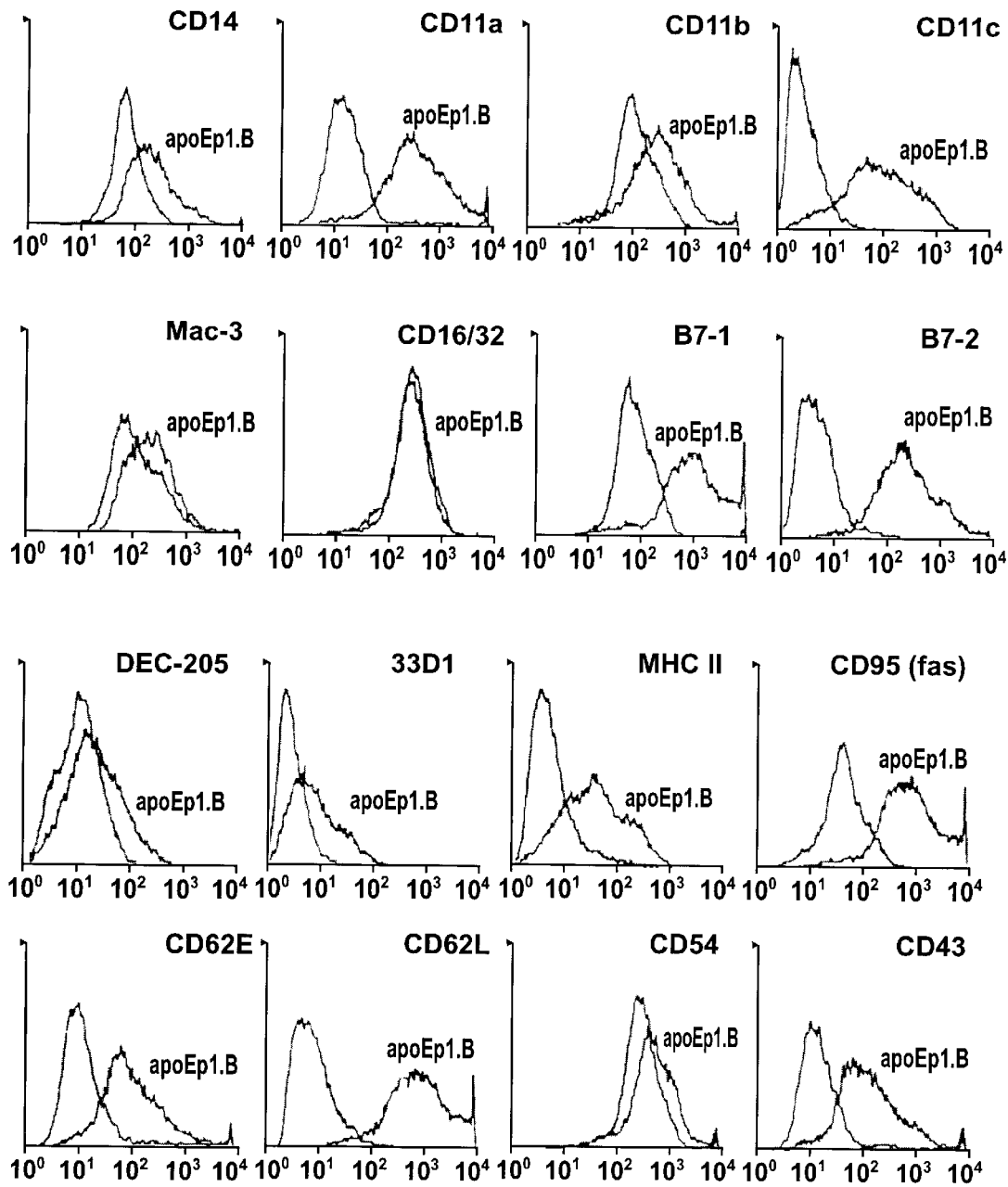
FIG. 3 is a FACS analysis of PU5-1.8 cells induced with apoEp1.B or apoEp1.D and stained with various markers.
Figure 4:
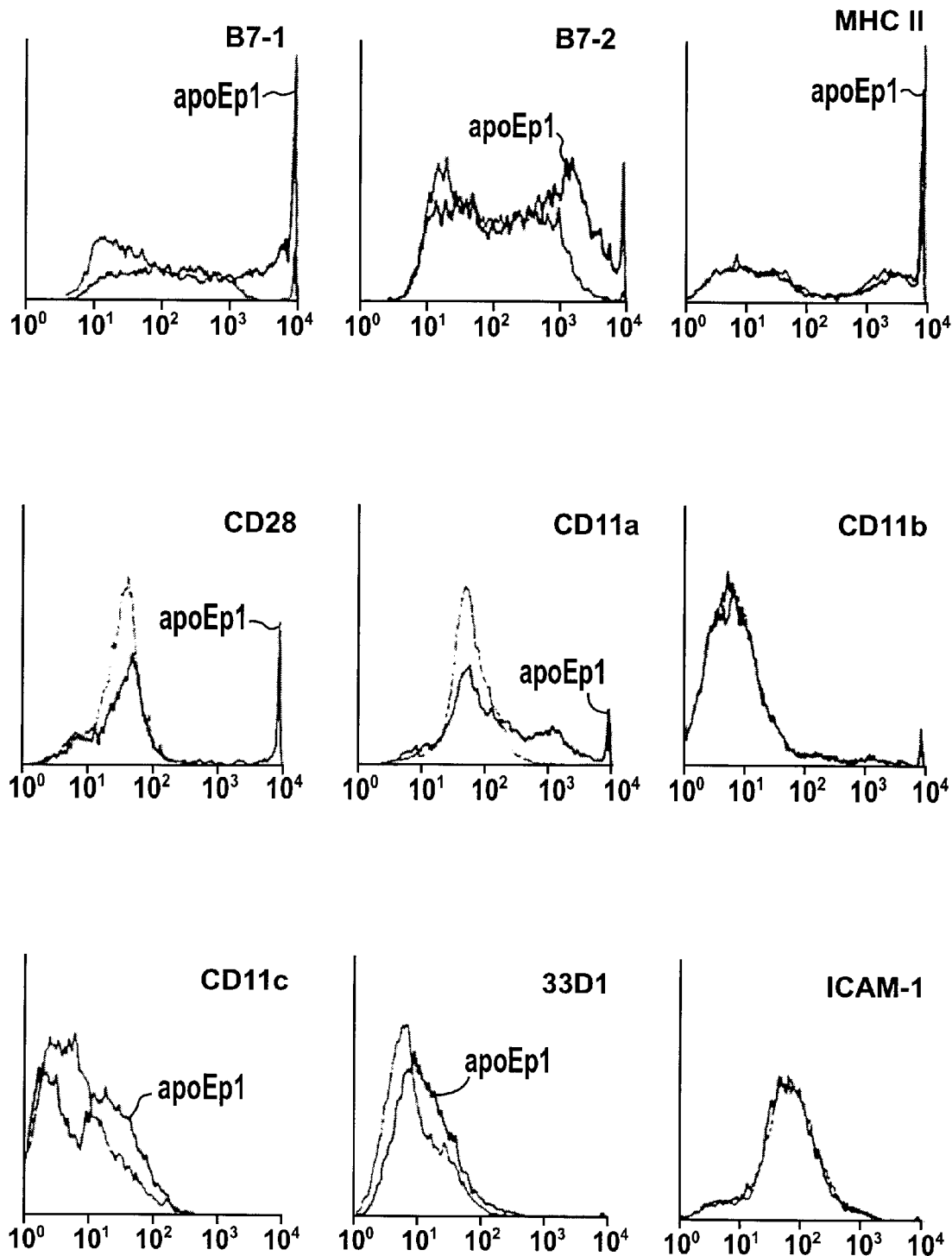
FIG. 4 shows FACS analysis of BAlb/c splenocytes incubated with 15 apoEp1.B or apoEp1.D.

Morphologically apoEp1.B-treated cells appeared DC-like. This was confirmed this by FACS analysis. Unprimed BALB/c splenocytes and PU5-1.8 cells were incubated for 24 hr with 100 µg/ml apoEp1.B or control peptide apoEp1.D and then stained for FACS analysis. Surface expression of CD14, CD11a, CD11b, CD11c, B7-1, B7-2, DEC-205, 33D1, MHC class 11, fas, CD40, CD62L (L-selectin) and CD43 (leukosialin) were increased above background on apoEp1.B-incubated PU5-1.8 cells after 24 hr incubation (FIGS. 3 and 4). With repeated experimentation, expression of Mac-3 and CD54 (ICAM-1) were found to be relatively variable.

Figure 5:
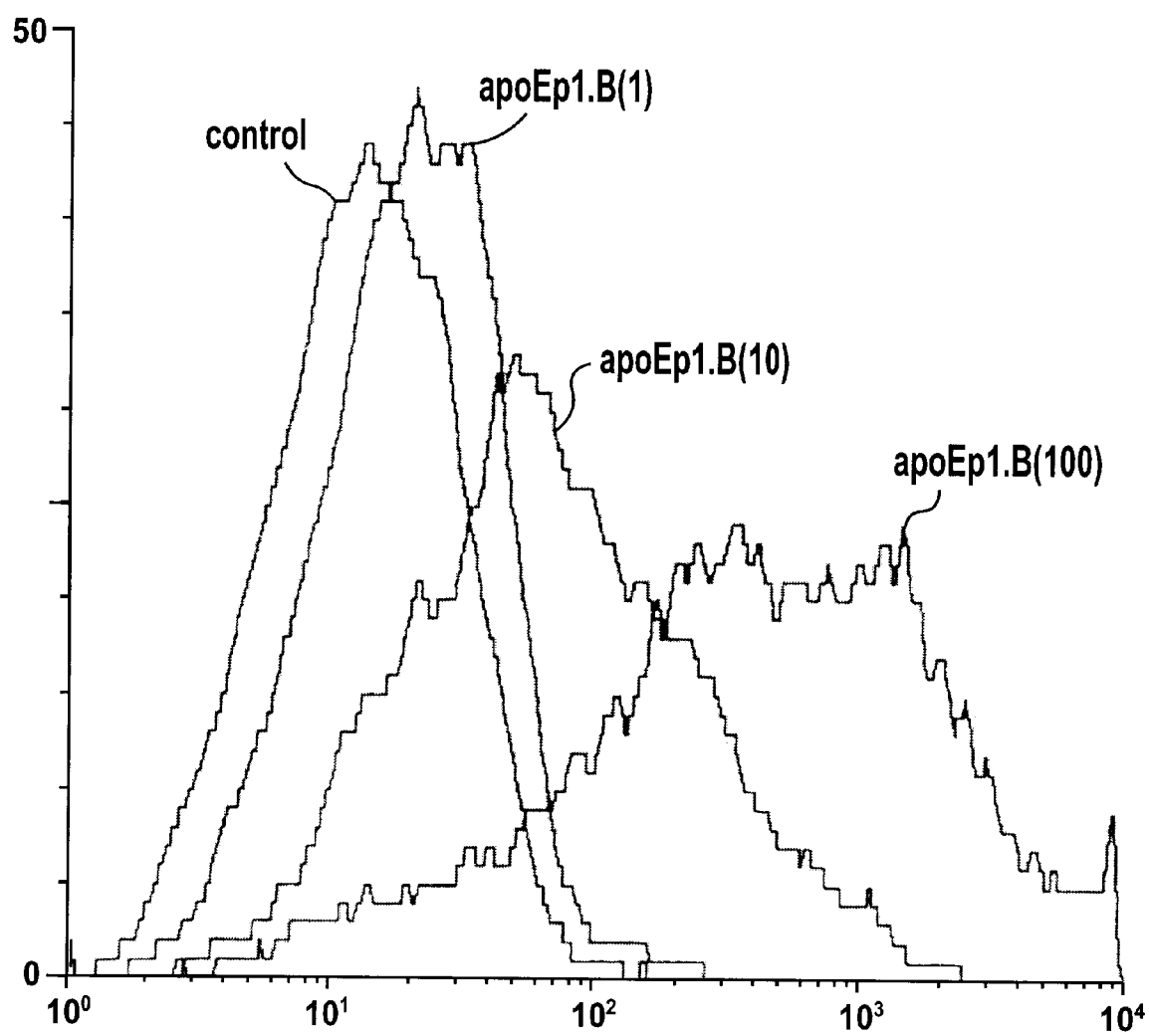
FIG. 5 shows a FACS analysis illustrating that apoEp1.B induced DC surface molecule expression is dose-dependent.

To assess whether apoEp1.B-induced phenotypic changes are dose-dependent, $10^5$ PU5-1.8 cells were incubated for 20 hr with 0 (medium), 1, 10 or 100 µg/ml apoEp1.B in 24-well plates and were then stained for FACS analysis. 10,000 events were collected. B7-1 marker is shown. The results, shown in FIG. 5 illustrate that 100 µg/ml apoEp1.B was found to be optimal, however, 1 µg/ml resulted in slight phenotypic changes.

Surface expression of B7-1, B7-2, MHC class 11, CD28, CD11a, CD11c and 33D1 were increased above background on apoEp1.B-incubated splenocytes after 24 hr incubation (see FIG. 4). There was also an increase in CD40 and a decrease in L-selectin (data not shown) on apoEp1-treated splenocytes. There were no changes in the expression of CD16/32 at any time.

Figure 6:
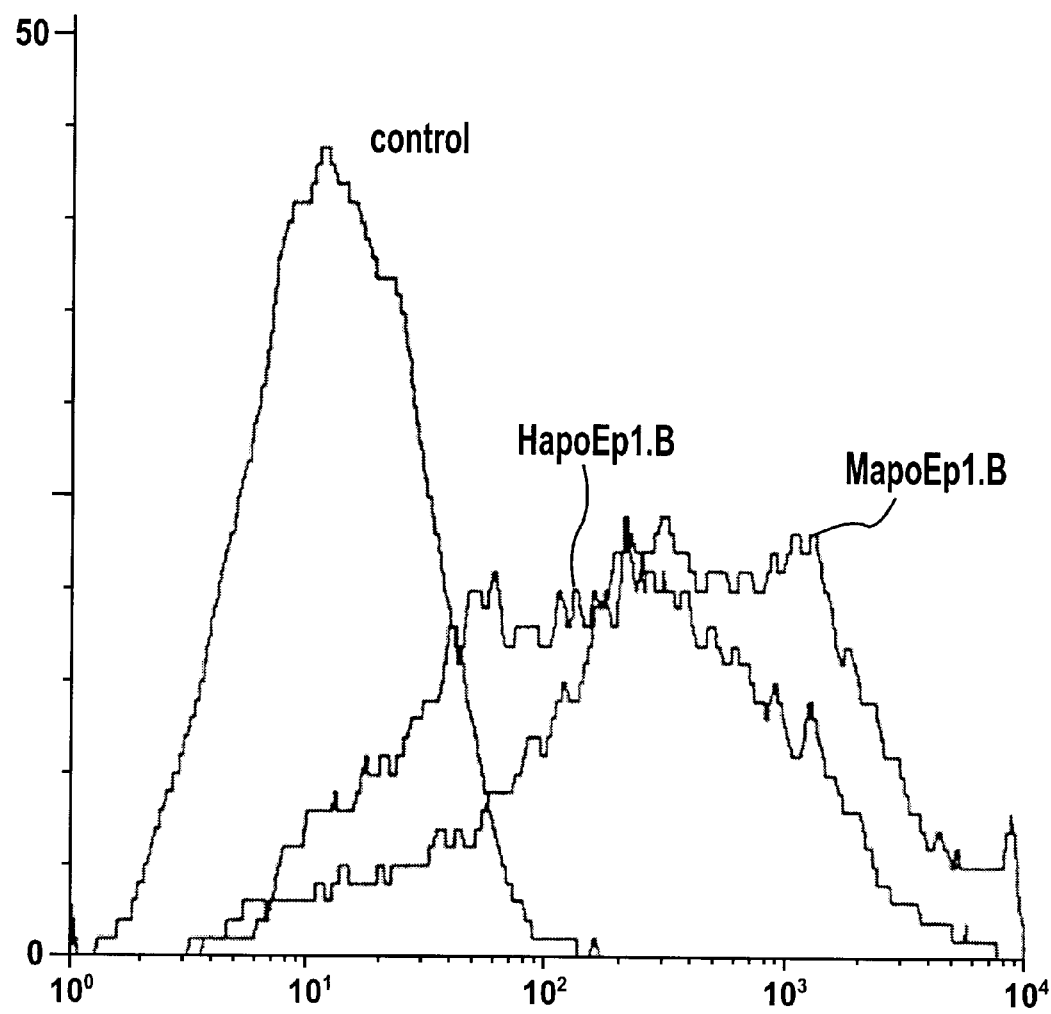
FIG. 6 shows a FACS analysis which demonstrates that apoEp1.B is not species-specific.
Figure 7:
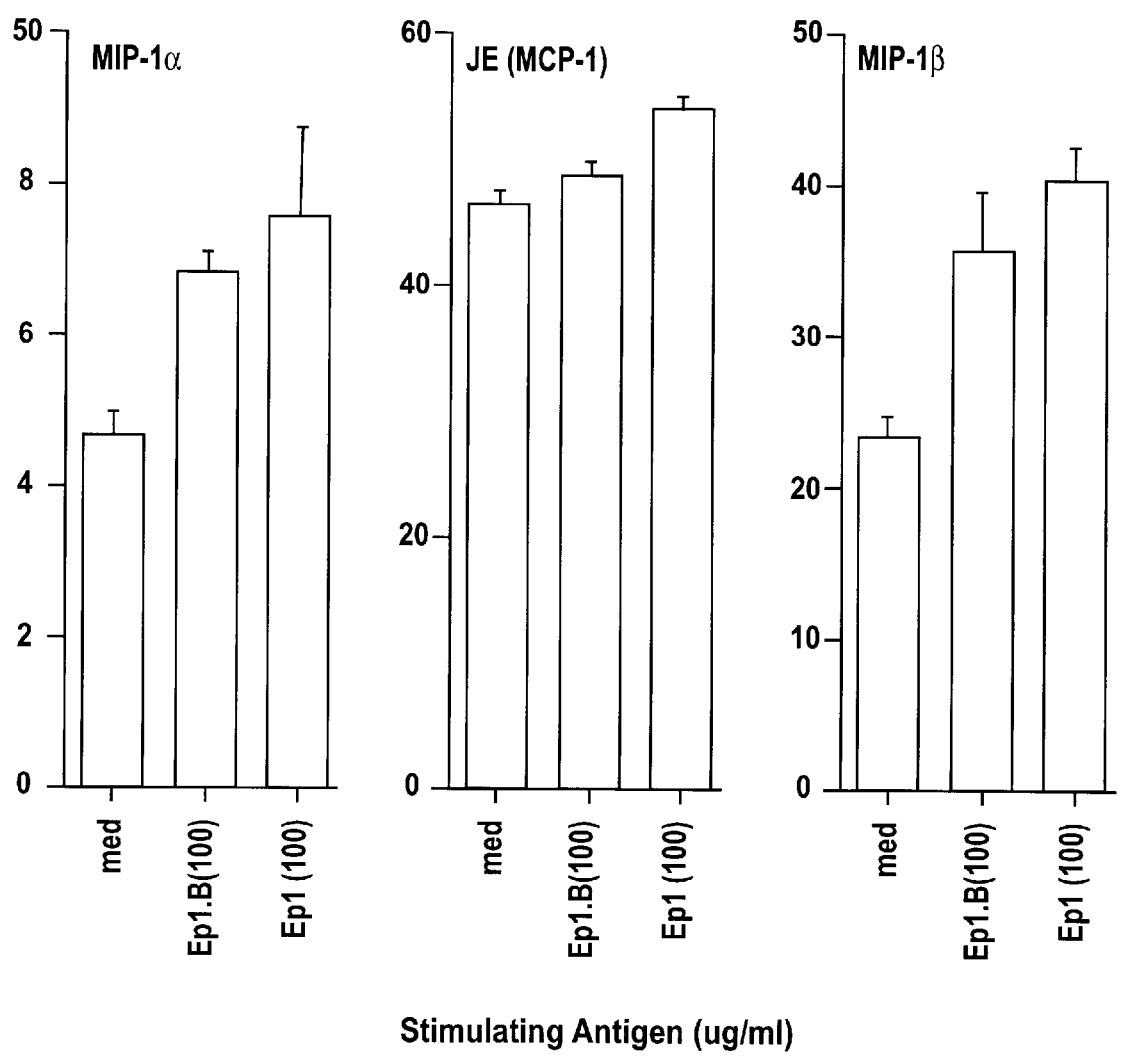
FIG. 7 are bar graphs demonstrating chemokine production from PU5-1.8 cells incubated with apoEp1.B, apoEp1 and a control.

ApoEp1.B Peptide-induced Differentiation and Activation is not Strain or Species-specific Unprimed B6 and NOD splenocytes were incubated with 100 µg/ml apoEp1.B or apoEp1.D to determine whether apoEp1.B was strain-specific. After 48 hr in culture, cells were stained for FACS analysis. B6 and NOD splenocytes responded to apoEp1.B with similar marker expression increase to that of BALB/c splenocytes (data not shown). Naive spleen cells from apoE deficient (apoE K.O.) mice were also tested to determine whether in vivo production of apoE had any influence on this effect. ApoE K.O. splenocytes also responded with a similar marker expression increase to that of BALB/c (data not shown). Since human apoEp1.B (HapoEp1.B) (239–252) peptide has a high degree of homology to murine apoEp1.B ($^{239}$T to $^{239}$A and 248I to $^{248}$A), species cross-reactivity was tested. Human monocytic cell line U-937 responded within 24 hr to 100 µg/ml apoEp1.B with similar, but less profound morphological and phenotypic changes to that of PU5-1.8 cells (FIG. 15). To determine whether the HapoEp1.B had a similar effect on murine cells, $10^5$ PU5-1.8 cells were incubated with 100 µg/ml HapoEp1.B or murine apoEp1.B for 24 hr. The cells were then stained for FACS analysis. HapoEp1.B induced cell clustering and an increase in similar markers to that of murine apoEp1.B, but to a lesser degree (B7-1 marker expression shown in FIG. 6).

ApoEp1.B Induces DC-like Cells When Injected Intraperitoneally

Figure 8A:
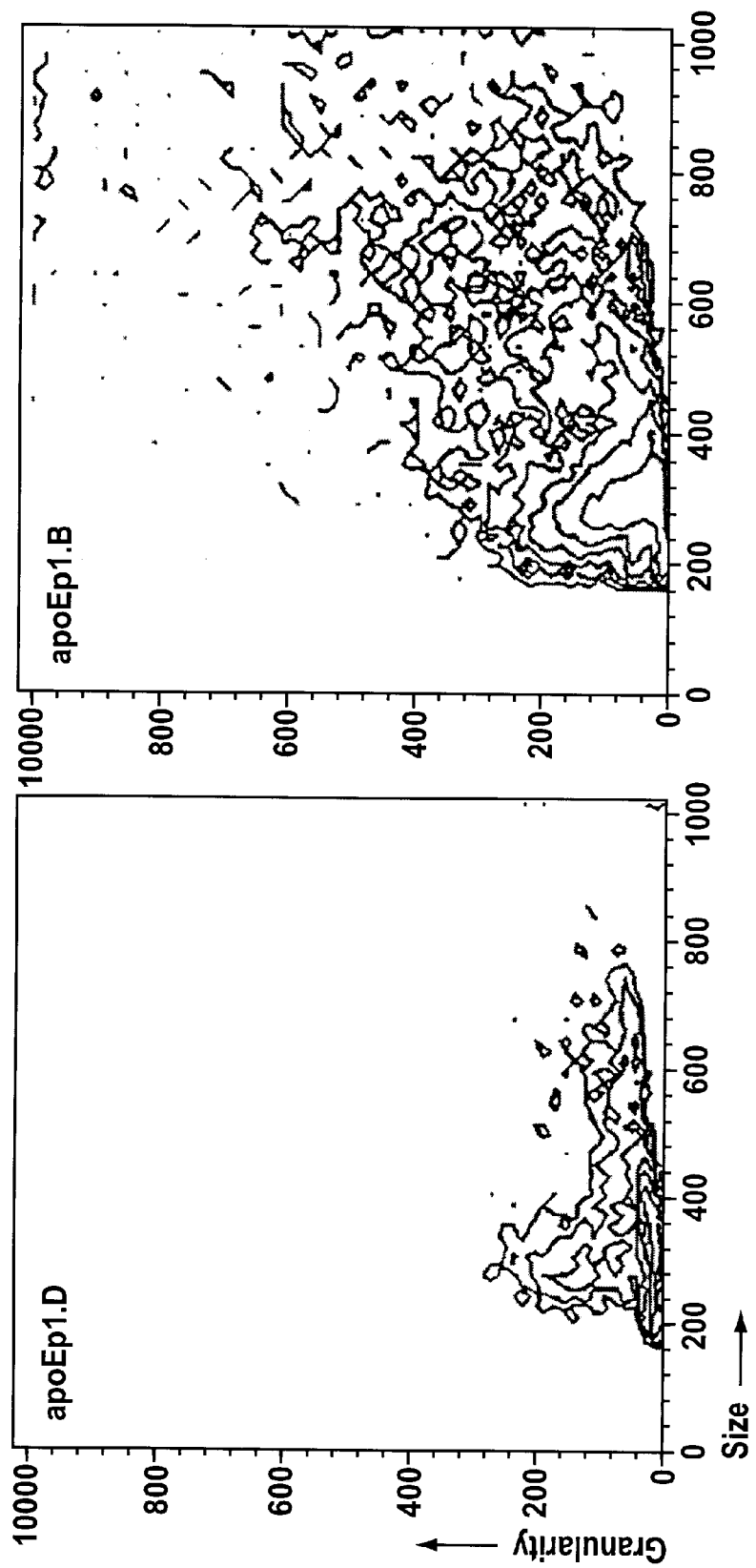
FIG. 8A is a FACS analysis showing SCC and FSC profiles of apoEp1.D and apoEp1.B primed PEC cells.
Figure 8B:
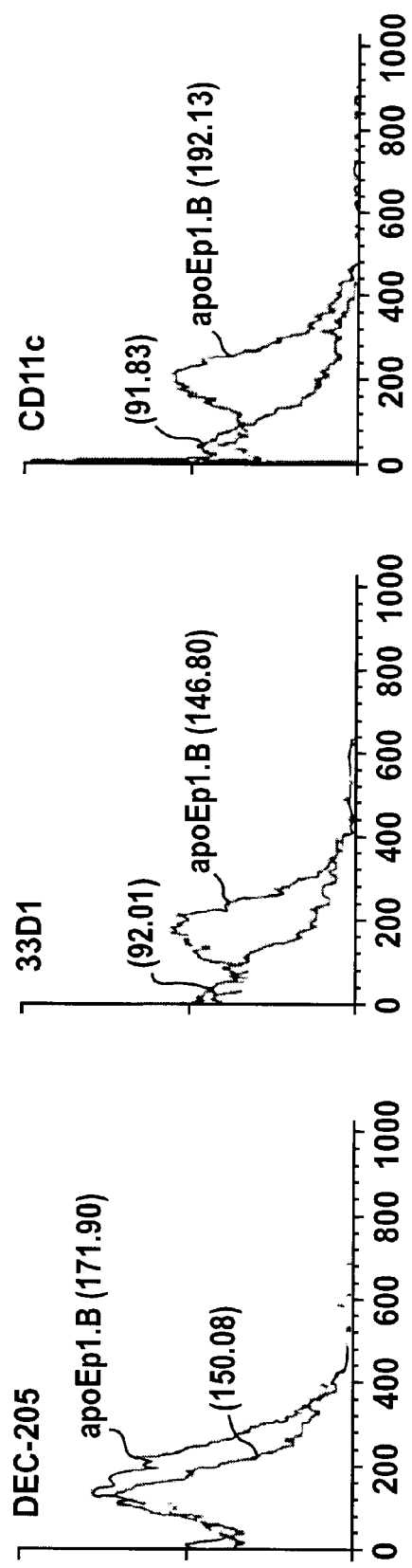
FIG. 8B is a FACS analysis showing surface marker expression of apoEp1.D (unlabelled peak) and apoEp1.B (labelled peak) primed PEC cells.

To assess whether apoEp1.B could induce DC-like cells in vivo, BALB/c mice were injected i.p. with 300 µg/ml apoEp1.B or apoEp1.D. After 48 hr PEC's were stained for FACS analysis. ApoEp1.B induced an increase in cell size and granularity (FIG. 8A) and an increase in surface expression of DEC-205, 33D1, CD11c, B7-1 and B7-2 (FIG. 8B). Unlabelled peaks correspond to apoEp1.D. Mean fluorescent intensity shown in brackets. The results demonstrate that apoEp1.B induces differentiation and activation of PECs in vivo similar to the in vitro system.

Figure 9:
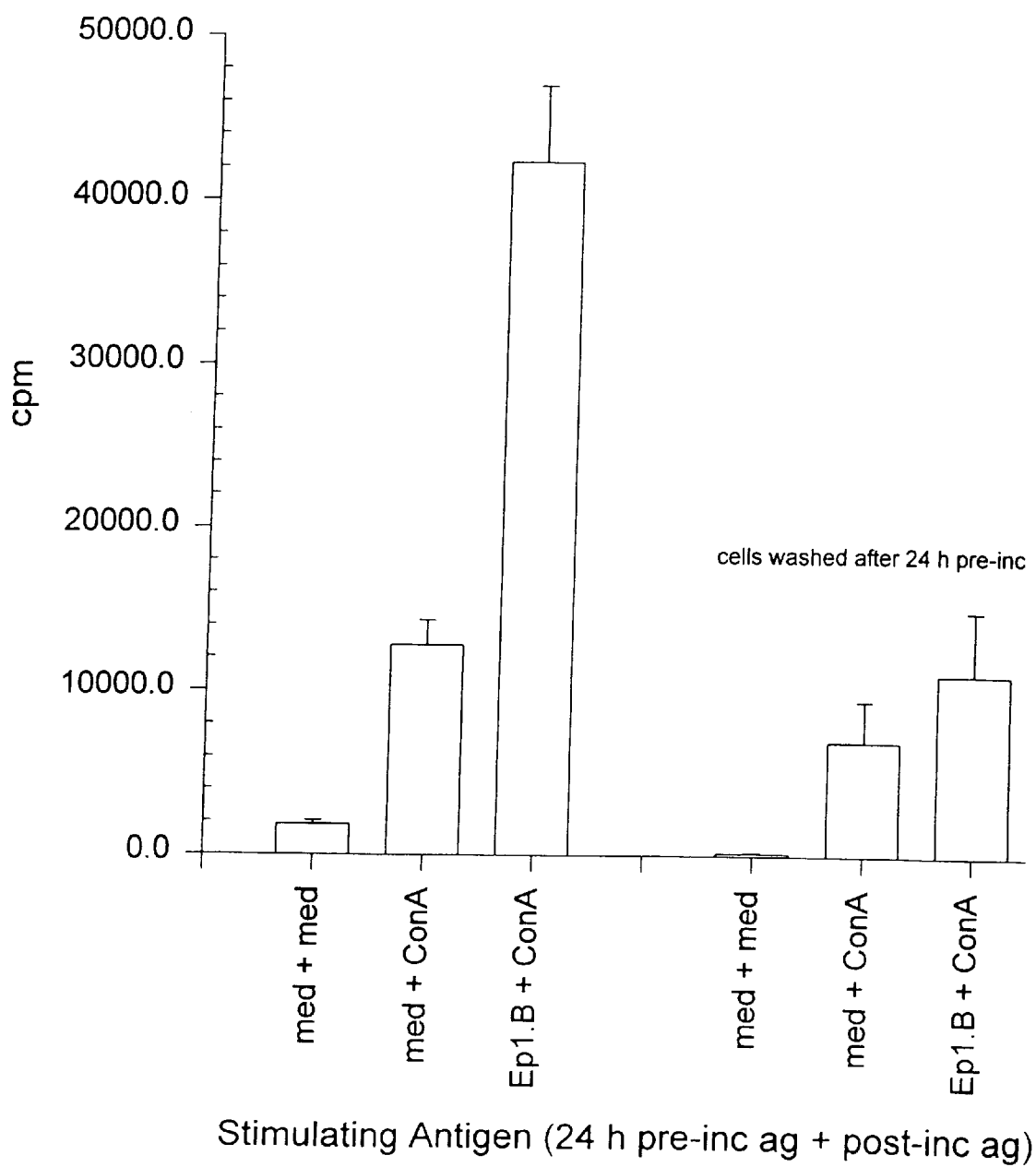
FIG. 9 is a bar graph showing activation of spleen cells in the presence of apoEp1.B and/or ConA.

To assess functional activation of apoEp1.B treated cells, BALB/c unprimed splenocytes were incubated with or without apoEp1.B (100µg/ml) in vitro for 24 hours. Cells (washed and unwashed) were stimulated with ConA for 12 hours and 3H was then added for an additional 12 hours. Cells were then harvested and readioactivity uptake counted. Results are presented as the mean of triplicate wells (cpm+/− SEM). As shown in FIG. 9, apoEp1.B treated cells respond to mitogen 3-fold higher than untreated cells.

Cytokines Produced After ApoEp1.B Immunization

ApoEp1.B or apoEp1.D-imrnmunized NOD lymph node cells were cultured for 48 hr in the absence of challenge antigen or exogenous cytokine. Cell supernatants were harvested and tested for cytokine content to assess whether apoEp1.B induced a Th1 or Th2 response. ApoEp1.B-primed cells secreted higher levels of IL-4 and lower levels of IL-2 than apoEp1.D primed cells (FIG. 12). There was no change in IFNγ.

T Cell Allostimulatory Activity of ApoEp1.B-induced DC

To measure the T cell allostimulatory or inhibitory ability of these DC's, $4 \times 10^4$ enriched BALB/c naive T cells were co-cultured with 40, 400, 4000 and 40,000 mitomycin C-treated NOD splenocytes which had been incubated with various stimualants for 3 d. T cell proliferation was measured following 3 days of co-culture by [$^3$H]-TdR incorporation. The results are shown in FIG. 12. Bars represent the mean of triplicate wells (cpm+/−S.D.). * and ** represent p<0.05 and p<0.001, respectively in 2-way ANOVA's compared to medium alone (nil) controls. ApoEp1.B-treated APC allostimulation was similar to that of untreated APC's at $4\times10^4$ APC's per well concentration, however, there was a slightly higher level of apoEp1.B-treated APC-T cell stimulation over untreated APC's at $4\times10^3$ and $4\times10^2$ APC's. There was a dramatic increase in allostimulation when APC's were pre-incubated with GM-CSF, particularly at $4\times10^3$ APC's per well. This increase was slightly, but significantly reduced when APC's were pre-incubated with GM-CSF plus apoEp1.B. The more striking result is depicted in FIG. 5B. APC's ($4\times10^3$) in all bars (except "T alone") have been untreated (nil) or pre-incubated with 100 μg/ml apoEp1.B, apoEp1.B+GM-CSF, or GM-CSF alone for 3 days prior to co-culture. Upon combining responder T cells with APC, various exogenous factors were added, including 20 μg/ml Con A and 5 μg/ml apoEp1.B. Very little proliferation was detected in wells containing T cells alone or APC alone. T cells proliferated well in response to Con A, however, when apoEp1.B was added, T cell allostimulation was completely abrogated.

DISCUSSION

It is known that monocytic cells can differentiate into DC's, however, GM-CSF has been long been thought to be essential for this effect (Scheicher et al., 1992). It has been shown here that a novel self peptide, apoEp1.B, alone induces DC's in vitro from both naive monocytic cells, and a murine cell line. These DC's possess the morphology and cell surface markers of classical DC's. ApoEp1.B also induces DC's in vivo upon apoEp1.B immunization. These DC's may favour a Th2 response as shown by an increase in IL-4 and a decrease in IL-2 production, and may therefore, be involved in split tolerance.

ApoEp1.B induced DC morphology of naive BALB/c splenocytes, enriched spleen monocytes (data not shown), monocytic cell lines PU5-1.8 (FIG. 1) and J77A4.1 in vitro (data not shown). Following only 2 hr incubation, apoEp1.B-treated cells started to detach from plastic plates and aggregated in suspension, a process characteristic of DC's. Since there was increased cell death, proliferation assays did not show an overall increase in cell number (data not shown). This is consistent with the loss of proliferation characteristic of cell differentiation.

ApoEp1.B-treatment of PU5-1.8 cells induced an increase in DC-specific markers, DEC-205, 33D1 and CD11c. Other markers that consistently increased were CD11a, B7-1, B7-2, MHC class II, fas, CD40 and L-selectin.

ApoEp1.B stimulation of splenocytes induced an increase in CD40, CD11a, CD11c, 33D1, B7-1, B7-2, MHC class II, fas and fasL expression at 24 hr. A similar profile was recorded following 72 hr post-apoEp1.B treatment (data not shown). These changes were not as dramatic as apoEp1.B-induced PU5-1.8 surface marker changes. This does not detract from the results obtained with PU5-1.8 cells as these cells are transformed and capable of rapid growth, cell division and protein synthesis.

Changes in B7 costimulatory molecules would inevitably alter T cell responses. Furthermore, an increase in MHC class II enables DC's to present peptides at a higher density which renders them more efficient at either T cell activation or tolerance. An increase in expression of adhesion molecules such as LFA-1 may enable DC's migration from various tissues to lymphoid organs where they present captured Ag.

In contrast to splenocytes, L-selectin expression on PU5-1.8 cells increases with apoEp1.B incubation (data not shown). L-selectin is rapidly downregulated on activated cells and thus the spleen cell data suggests that apoEp1.B activates these cells. These conflicting results are not extraordinary when considering that PU5-1.8 cells are transformed as well as a homogenous population. Heterogeneous cell-cell interactions as well as paracrine stimulatory and inhibitory factors that affect immune responses may explain some of the differences between spleen and PU5-1.8 cells. Furthermore, transformed PU5-1.8 cells may lack mechanisms necessary for L-selectin downregulation, such as specific proteases for L-selectin cleavage. CD28 expression on splenocytes is also increased slightly with apoEp1.B treatment.

A slight increase in macrophage differentiation markers CD14 and Mac-3, indicates that maturation of macrophages may be also occurring in apoEp1.B-treated cultures. Whether these cells then develop into DC'S, apoptose or remain as macrophages is unknown.

Following i.p. injection, apoEp1.B induced an increase in PEC size and granularity and an increase in DC-specific markers, DEC-205, 33D1 and CD11c as well as B7-1 and B7-2. Therefore, injection of apoEp1.B i.p. induces PEC's to express a similar DC-like phenotype compared to in vitro experiments. The increase in DC marker expression is not as pronounced as it was in vitro, probably due to the dilution and/or clearance of apoEp1.B peptide in vivo. However, since DC's are efficient at T cell stimulation or inhibition, even a modest increase in number may have a profound effect on an immune response.

The treatment of NOD mice with apoEp1.B stimulated an increase in IL-4 secretion, presumably by Th2-like cells and a decrease in IL-2. The immunization of mice with apoEp1.B also induced an increase in DC's.

Whether apoEp1.B is a naturally cleaved product of apoE is unclear but doubtful. ApoEp1.B binds I-$A^d$ with a similar affinity to that of. the original apoEp1 peptide (which does not induce DC's), yet was not eluted in elution experiments, it is therefore, probably not naturally cleaved a high levels.

Here we show that apoEp1.B, stimulates mo/ma activation. In addition, apoEp1.B induces DC's that may favour a Th2-like response. These DC's may be partially activated or not fully mature, fully activated or induced to full maturity by inflammatory signals.

Example 2

ApoEp1.B Inhibits Atherosclerotic Plaque Development

Figure 10A:
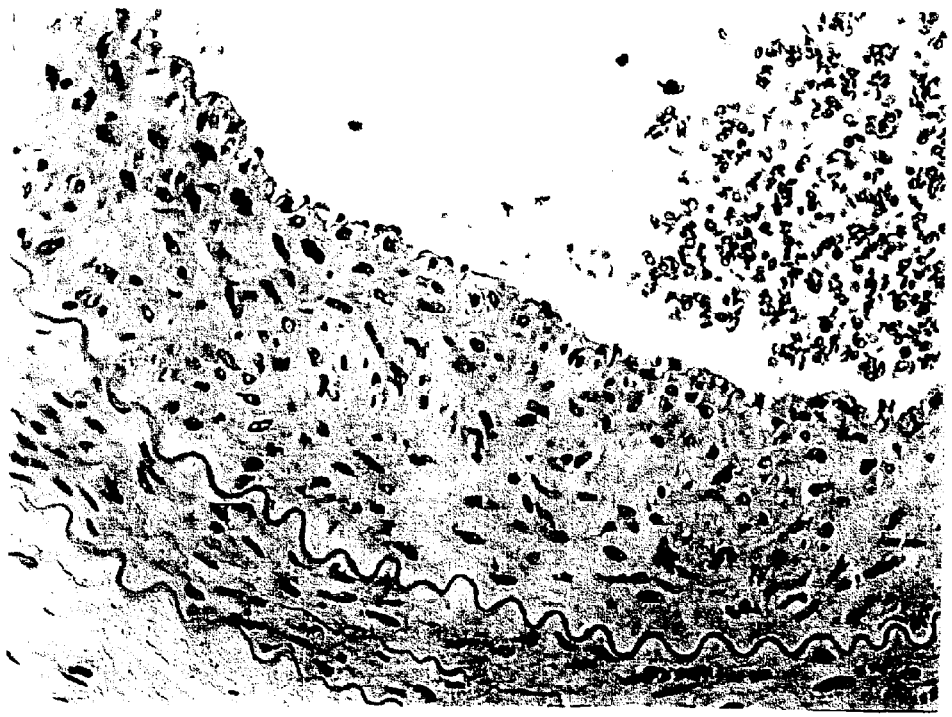
FIG. 10 shows a section of iliofemoral arteries: (A) untreated, no surgery.
Figure 10B:
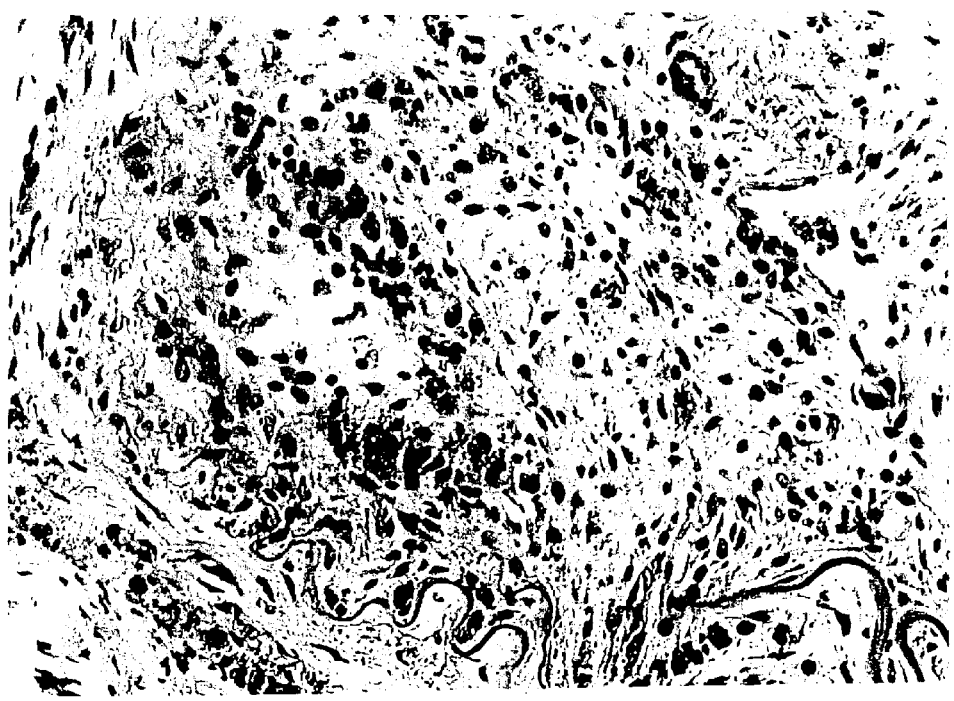
Figure 10C:
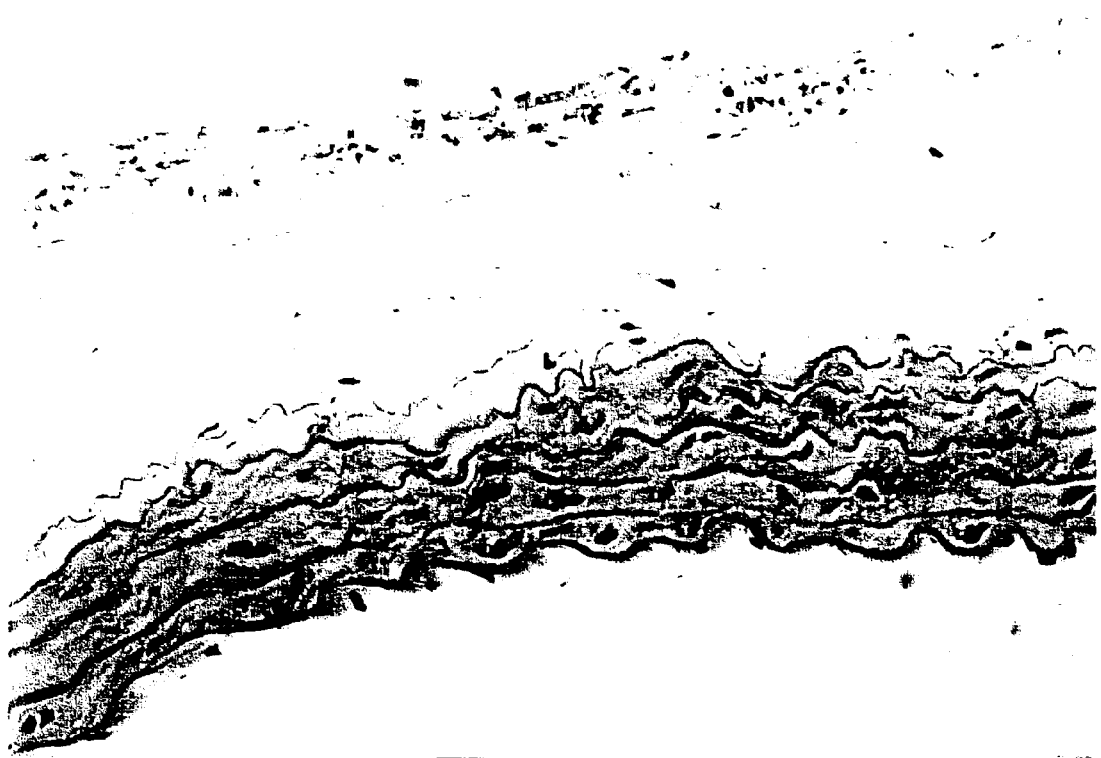

To investigate the role of apoEp1.B peptide in inflammation, particularly in response to arterial injury, a balloon angioplasty injury model which has been well characterized by Dr. Alex Lucas (Lucas et al. 1996 Circ. 94:2898–900) was used. 300 μg/ml of apoEp1 or apoEp1.B peptide were infused intra-arterially immediately prior to angioplasty at the site of injury in the iliofemoral artery of the rat. Positive control SERP-1 and negative control saline alone were also used. The rats were monitored carefully and euthanized 6 weeks after treatment and iliofemoral arteries were assessed for plaque development by histochemistry. Careful measurement of arterial thickness and lumen size showed apoEp1.B (500 μg) peptide reduced lesion size in this model. In fact, in many of the apoEp1.B treated rats, no plaque was detected. No adverse effects were observed in apoEp1.B treated rats. The results are presented in Table 3 and FIG. 10.

Example 3

ApoEp1.B Immunization Protects Mice From Diabetes 8 female 8 week old NOD mice were immunized with 250 μg apoEp1.B peptide emulsed in IFA in one footpad. 6 negative control mice were immunized with saline in IFA. Mice were monitored for a following 4 months and their urine glucose tested to assess diabetes development. At the 8 month end date, all 8 apoEp1.B immunized mice still remain diabetes free. 4 of the 6 mice treated with saline in IFA are deceased due to diabetes. The results, shown in FIG. 14, demonstrate that apoEp1.B immunization protects diabetes prone mice.

Example 4

ApoEp1.B-immunization Induces Th2-like Cells

NOD mice were immunized via the footpad with 200 μg/ml apoEp1.B or apoEp1 D peptide in IFA. Draining lymph nodes were removed following 7 days and cells cultured in 96-well microtiter plates in the absence of further stimulation. Cell culture supernatants were harvested at 48 hr and tested for cytokine content. The results, shown in FIG. 11, demonstrate that apoEp1.B immunization induce Th2-like cells. (Results of IL-2, IL-4 and IFNγ are presented as the mean of triplicate wells (O.D.+/−SEM). * represents $p<0.001$ in 2-way ANOVA's compared to apoEp1.D-treated controls.)

To determine whether the Th2 response induced by apoEp1.B immunization influenced IDDM incidence, 10 female 8 week old NOD mice were immunized with 200 μg/ml apoEp1.B and 10 mice with negative control apoEp2 emulsed in IFA in one footpad. Mice were monitored for the following 8 months and their urine and blood glucose tested for disease onset. At 10 months, 7 of 10 apoEp1.B-immunized mice remain diabetes free, whereas, 1 of 10 apoEp2-treated mice remaines disease-free. (FIG. 13A).

Example 5

ApoEp1.B Immunization Protects NOD.SCID Mice From Adoptively Transferred Diabetes To test the protective effect of apoEp1.B in an alternative model of IDDM, $10^7$ diabetogenic splenocytes were adoptively transferred to 20 NOD.SCID mice. 10 of these mice were immunized with 200 μg/ml apoEp1.B, the other with 200 μg/ml apoEp2, the other with 200 μg/ml apoEp2. All 10 negative controls have succumbed to disease after 5 weeks. 5 of the 10 apoEp1.B mice remain diabetes-free at 9 weeks (FIG. 13B).

Discussion of Results From Examples 3,4 and 5

Since a Th2 response can be protective in the NOD model of IDDM and since apoEp1.B immunization of NOD mice favours a Th2 type response (see FIG. 11), apoEp1.B was tested for disease protection in these mice. ApoEp1.B/IFA immunization significantly delayed disease onset in NOD mice and in adoptively-transferred NOD.Scid mice. ApoEp1.B-protected mice had slightly less islet infiltration as compared to unprotected mice (data not shown), indicating that apoEp1.B protection may involve the induction of regulatory cells rather than deletion of destructive effector cells.

APC's from NOD mice are thought to have functional and/or differentiation defects (Serreze et al., 1988, Serreze et al., 1993). Since NOD Th2 cells are more dependent on B7 costimulation than Th1 cells (Rulifson et al., 1997), a proinflammatory Th1 response may predominate in these mice by default. Consistent with this are studies demonstrating that Th2 cell hyporesponsiveness intrinsic to NOD mice (Zipris 1991a and 1991b) is reversible either by IL-4 (Rapoport et al., 1993, Mueller et al., 1996, Cameron et al., 1997) or CD28 (Arreaza et al., 1997) administration in vivo. Anti-CD28 treatment is thought to promote Th2 survival and expansion. Furthermore, costimulation deficient mice (CD28−/−) display more severe IDDM (Rulifson et al., 1997).

It is unclear what role DC's play in IDDM, however, the importance of DC's in disease is emphasized by the DC K.O. mouse (RelB−/−). These mice display aggressive multi-organ infiltration and inflammation. Another group reported that pancreatic DC's can induce disease protection upon transfer (Clare-Salzler et al., 1992). These findings suggest that DC's may play a protective role in IDDM. Furthermore, Voorbij et al. (1989) showed that DC's were the first cells to accumulate around pancreatic islets in the spontaneously diabetic BB rat model, followed by lymphocytes.

Whether the induction of DC's upon apoEp1.B injection has a direct effect on disease protection is unknown, however, the resulting Th2 response may be mediating protection. It is proposed that apoEp1.B immunization stimulates DC differentiation with an increase in B7 costimulatory molecules. These more efficient APC's, capable of stronger costimulation, rescue IL-4 producing Th2 cell responsiveness in diabetes-prone mice. This in turn reduces disease incidence. Alternatively or additionally, apoEp1.B may act directly on T cells, increasing CD28 expression and/or lowering the threshold for stimulation. Since Th1 cells are already stimulated in NOD mice, protective Th2 or Th3 cell stimulation may be preferentially restored. Consistent with this statement is the data showing no change in IFN production, yet an increase in IL-4.

Since the lack of Th2 cell responsiveness intrinsic to NOD mice (Zipris 1991a and 1991b) is reversible, it is proposed the apoEp1.B immunization rescues Th2 responsiveness in diabetes-prone mice, which in turn reduces disease incidence. Since T cells require APC's for stimulation, we speculate that apoEp1.B stimulates a Th2-inducing APC, possible of the DC phenotype. Irrespective of mechanism, apoEp1.B may offer a potential self peptide therapy for diabetes as well as other Th1-mediated autoimmune diseases.

Example 6

Modifications to ApoEp1.B Sequence

Various amino acid substitutions and elongations were made to the apoEp1.B peptide as illustrated in Tables 1 and 2. The modified peptides were incubated at 100 μg/ml with $10^5$ PU5-1.8 cells for 20 hours. The cells were stained with B7-1 for FACS analysis. The results demonstrate that some, but not all, single a.a. substitutions, elongations or deletions can decrease or abrogate apoEp1.B effects (see Table 1 and 2 and FIGS. 16 and 18). This supports the notion that there is a receptor to which apoEp1.B binds and certain a.a. changes decrease peptide-receptor affinity. The deletion of $239^T$ results in a greatly reduced effect on surface marker changes. However, the substitution of this same a.a. with an alanine (as in the sequence of HapoEp1.B) has only a slightly reduced effect compared to apoEp1.B. Therefore, the length of apoEp1.B is likely important in receptor binding. It also appears that the structural integrity resides in the carboxy terminal region of the apoEp1.B peptide as even slight changes in that region decreases or abolishes the activity of the peptide.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

IL-4 prevents insulitis and insulin-dependent diabetes mellitus in nonobese diabetic mice by potentiation of regulatory T helper-2 cell function. J. Immunol, Nov. 15, 159(10):4686–92.

Caux, C., Dezutter-Dambuyant, C., Schmitt, D., and Banchereau, J. (1992). GM-CSF and TNF-a cooperate in the generation of dendritic Langerhans cells. Nature 360, 258–261.

Caux, C., Massacrier, C., Vanbervliet, B., Dubois, B., Van Kooten, C., Durand, I., and Banchereau, J. (1994). Acti-

TABLE 1

ApoEp1.B Elongations and Truncations

| Name | Sequence | Residues | DC Marker Changes |
|---|---|---|---|
| apoEp1 | EEQ TQQ IRL QAE IFQ AR (SEQ.ID.NO.:9) | 236–252 | slight |
| apoEp1.Ba | EQ TQQ IRL QAE IFQ AR (SEQ.ID.NO.:10) | 237–252 | − |
| apoEp1.Bb | Q TQQ IRL QAE IFQ AR (SEQ.ID.NO.:7) | 238–252 | ++ |
| apoEp1.B | TQQ IRL QAE IFQ AR (SEQ.ID.NO.:1) | 239–252 | +++++ |
| apoEp1.Bc | QQ IRL QAE IFQ AR (SEQ.ID.NO.:8) | 240–252 | ++ |
| apoEp1.Bd | Q IRL QAE LFQ AR (SEQ.ID.NO.:11) | 241–252 | − |

TABLE 2

ApoEp1.B Amino Acid Substitutions

| Name | Sequence | Residues | DC Marker Changes |
|---|---|---|---|
| apoEp1.B A$^{240}$ | TAQ IRL QAE IFQ AR (SEQ.ID.NO.:3) | 239–252 | +++ |
| apoEp1.B A$^{241}$ | TQA IRL QAE IFQ AR (SEQ.ID.NO.:4) | 239–252 | +++++ |
| apoEp1.B A$^{242}$ | TQQ ARL QAE IFQ AR (SEQ.ID.NO.:5) | 239–252 | ++ |
| apoEp1.B A$^{243}$ | TQQ IAL QAE IFQ AR (SEQ.ID.NO.:6) | 239–252 | +++ |
| apoEp1.B A$^{244}$ | TQQ IRA QAE IFQ AR (SEQ.ID.NO.:12) | 239–252 | − |
| apoEp1.B A$^{245}$ | TQQ IRL AAE IFQ AR (SEQ.ID.NO.:13) | 239–252 | − |
| apoEp1.B A$^{247}$ | TQQ IRL QAA IFQ AR (SEQ.ID.NO.:14) | 239–252 | − |
| apoEp1.B A$^{248}$ | TQQ IRL QAE AFQ AR (SEQ.ID.NO.:15) | 239–252 | − |
| apoEp1.B A$^{249}$ | TQQ IRL QAE IAQ AR (SEQ.ID.NO.:16) | 239–252 | − |
| apoEp1.B A$^{250}$ | TQQ IRL QAE IFA AR (SEQ.ID.NO.:17) | 239–252 | − |
| apoEp1.B A$^{239,240}$ | AAQ IRL QAE IFQ AR (SEQ.ID.NO.:18) | 239–252 | − |
| apoEp1.B A$^{240,241}$ | TAA IRL QAE IFQ AR (SEQ.ID.NO.:19) | 239–252 | − |
| apoEp1.B A$^{239-241}$ | AAA IRL QAE IFQ AR (SEQ.ID.NO.:20) | 239–252 | − |
| human apoEp1.B | AQQ IRL QAE AFQ AR (SEQ.ID.NO.:2) | 239–252 | ++++ |

TABLE 3

| | Lumen Area (mean +/− S.E.) | Plaque Thickness (mean +/− S.E.) | Plaque area (mean +/− S.E.) |
|---|---|---|---|
| saline | 0.027 +/− 0.012 | 0.139 +/− 0.028 | 0.059 +/− 0.010 |
| apoEp1.B | 0.156 +/− 0.020 | 0.003 +/− 0.003 | 0.002 +/− 0.002 |
| P-value | <.0001 | <.0001 | <.0001 |

FULL CITATIONS FOR REFERENCES REFERRED TO IN THE SPECIFICATION

Arreaza, G. A., Cameron, J. J., Jaramillo, A., Gill, B. M., Hardy, D., Laupland, K. B., Rapoport, M. J., Zucker, P., Chakrabarti, S., Chensue, S. W., Qin, H. Y., Singh, B., Delovitch, T. L. (1997) Neonatal activation of CD28 signaling overcomes T cell energy and prevents autoimmune diabetes by an IL-4-depednent mechanism. J. Clin Invest. Nov 1, 100(9):2243–53.

Cameron, M. J., Arreaza, G. A., Zucker, P., Chensue, S. W., Strieter, R. M., Chakrabarti, S., Delovitch, T. L. (1997)

vation of human dendritic cells through CD40 cross-linking. J. Exp. Med. 180,1263–1272.

Christianson, S. W., Shultz, L. D., and Leiter, E. H. (1993). Adoptive transfer of diabetes into immunodeficient NOD-scid/scid mice—relative conttributions of CD4+ and CD8+ T-cells from diabetic versus prediabetic NOD.NON-Thy-1a donors. Diabetes 42, 44–55.

Clare-Salzler, M. J., Brooks, J., Chai, A., Van Herle, K., and Anderson, C. (1992). Prevention of diabetes in nonobese diabetic mice by dendritic cell transfer. J. Clin. Invest. 90, 741–748.

Daniel, D., Gill, R. G., Schloot, N., and Wegrnann, D. (1995). Epitope specificity, cytokine production profile and diabetogenic activity of insulin-specific T cell clones isolated from NOD mice. Eur J Immunol. 25,1056–1062.

Delovitch, T. L., and Singh, B. (1997). The nonobese diabetic mouse as a model of autoimmune diabetes: immune dysregulation get the NOD. Immunity 7, 727–738.

Dyer, C. A., Smith, R. S., and Curtiss, L. K. (1991). Only multimers of a synthetic peptide of apolipoprotein E are biologically active. J. Biol. Chem. 266, 15009–15015.

Fitch, F. W. McKisic, M. D., Lancki, D. W., and Gajewski, T. F. (1993). Differential regulation of murine T lymphocyte subsets. Annu Rev Inmmunol. 11, 29–48.

Finkelman, F. D., Lees, A., Bimbaum, R., Gause, W. C., and Morris, S. C. (1996). Dendritic cells can present antigen in vivo in a tolerogenic or immunogenic fashion. J. Immunol. 157, 1406–1414.

Galy, A., Travis, M., Cen, D., and Chen, B. (1995). Human B, T, natural killer and dendritic cells arise from a common bone marrow progenitor cell subset. Immunity 3, 459–473.

Gao, J.-X., Madrenas, J., Zeng, W., Zhong, R., and Grant, D. (1997). Generation of dendritic cell-like antigen-presenting cells in long-term mixed leucocyte culture: phenotypic and functional studies. Immunology. 91, 135–144.

Grosjean, I., Caux, C., Bella, C., Berger, I., Wild, F., Banchereau, J., and Kaiserlian. (1997). Measles virus infects human dendritic cells and blocks their allostimulatory properties for CD4+ T cells. J. Exp. Med. 186, 801–812.

Groux, H., Bigler, M., de Vries J. E., and Roncarolo,M. (1996). Interleukin-10 induces a long-term antigen-specific anergic state in human CD4+ T cells. J. Exp. Med 184: 19–29.

Haskins, K., and McDuffie, M. (1990). Acceleration of diabetes in young NOD mice with a CD4+ islet-specific T cell clone. Science 249, 1433–1436.

Hsieh, C.-S., Heimberger, A. B., Gold, J. S., O'Garra, A., and Murphy, K.M. (1992). Differential regulation of T helper phenotype development by interleukins 4 and 10 in alpha beta T cell-receptor transgenic system. Proc. Natl. Acad. Sci. USA 89, 6065–6069.

Hsu, F. J., Benike, C., Fagnoni, F., Liles, T. M., Czerwinski, D., Taidi, B., Engleman, E. G., and R Levy. 1996. Vaccination of patients with B-cell lymphoma using autologous antigen-pulsed dendritic cells. Nat. Med. 2:52–8.

Hunt, D., H. Michel, J. S. Dickinson, J. Shabanowitz, A. L. Cox, K. Sakaguchi, E. Appella, H. M. Grey, and A. Sette. 1992. Peptides presented to the immune system by murine class II major histocompatibility complex IAd. Science 256:1817–1820.

Kalinski, P., Hilkens, C. M. U., Snijders, F., Snijdewint, F. G. M., and Kapsenberg, M. L. (1997). IL-12-deficient dendritic cells, generated in the presence of prostaglandin E2, promote type 2 cytokine production in maturing human naive T helper cells. J. Immunol. 159, 28–35.

Katz, J. D., Benoist, C., and Mathis, D. (1995). T helper subsets in insulin-dependent diabetes. Science 268, 1185–1188.

Kelly, M. E., M. A. Clay, M. J. Mistry, H. M. HsiehLi, and J. A. K. Harmony. 1994, Apolipoprotein E inhibition of proliferation of mitogenactivated T lymphocytes: production of interleukin 2 with reduced biological activity. Cell Immunol. 159:124–139.

Kuchroo, V. K., Das, M. P., Brown, J. A., Ranger, A. M., Zamvil, S. S., Sobel, R. A., Weiner, H. L., Nabavi, N., and Glimcher, L. (1995). B7-1 and B7-2 costimulatory molecules activate differentially the Th1/Th2 developmental pathways: application to autoimmune disease therapy. Cell 80, 707–718.

Liblau, R. S., Singer, S. M., and McDevitt, H. O. (1995). Th1 and Th2 CD4+ T cells in the pathogenesis of organ-specific autoimmune diseases. Immunol Today 16, 34–38.

Lynch, D. H., Andreasen, A., Maraskovsky, E., Whitmore, J., Miller, R., and Schuh, C. L. (1997). Flt3 ligand induces tumor regression and antitumor immune responses in vivo. Nat Med. 3, 625–631.

MacNeil, D., Fraga, E., and B. Singh. 1993. Characterization of murine T cell responses to peptides of the variable region of self T cell receptor chains. J. Immunol. 151:4045.

Mahley, R. W. 1988. Apolipoprotein E: cholesterol transport protein with expanding role in cell biology. Science 240:622.

Maraskovsky, E., Brasel, K., Teepe, M., Roux, E. R., Lyman, S. D., Shortman, K., and H. J. McKenna. 1996. Dramatic increase in the numbers of functionally mature dendritic cells in Flt3 ligand-treated mice: multiple dendritic dell subpopulations identified. J. Exp. Med. 184:1953–1962.

Mayordama, J. I., Zorina, T., Storkus, W. J., Zitvogel, L., Celluzzi, C., Falo, L. D., Melief, C. J., Ildstad, S. T., Kast, W. M., Deleo, A. B., et. Al 1995. Bone marrow-derived dendritic cells pulsed with synthetic tumour peptides elicit protective and therapeutic antitumour immunity. Nat. Med. 12:1297–302.

Mosmann, T. R., and Coffman, R. L. (1989). TH1 and TH2 cells: different patterns of lymphokine secretion lead to different functional properties. Annu. Rev. Immunol. 7, 145–173.

Mueller, R., Krahl, T., and Sarvetnick, N. (1996). Pancreatic expression of interleukin-4 abrogates insulitis and autoimmune diabetes in NOD mice. J. Exp. Med. 184, 1093–1099.

Pennline, K. J., Roque-Gaffney, E., and Monahan, M. (1994). Recombinant human IL-10 prevents the onset of diabetes in the nonobese diabetic mouse. Clin. Immunol. Immunopathol. 71, 169–175.

Pepe, M., and L. Curtiss. 1986. Apolipoprotein E is a biologically active constituent of the normal immunoregulatory lipoprotein, LDLIn. J. Immunol. 136:3716.

Peters, J. H., Gieseler, R., Thiele, B., and Steinbach, F. 1996. Dendritic cells: from ontogenetic orphans to myelomonocytic descendants. Immunol. Today. 6:273–278.

Powrie, F., and Coffman, R. L. (1993). Cytokine regulation of T-cell function: potential for therapeutic intervention. Imnmunol. Today 14, 270–274.

Rapoport, M. J., Zipris, D., Lazarus, A. H., Jaramillo, A., Speck, E., and Delovitch, T. L. (1993), IL-4 reverses thymic T cell proliferative unresponsiveness and prevents diabetes in NOD mice. J. Exp. Med. 178,87–99.

Rider B. J., Fraga, E., Yu Q. and Singh B. (1996). Immune responses to self-peptides naturally presented by murine class II major histocompatibility complex molecules. Mol. Immunol. 33, 625–633.

Romagnani, S. (1992). Human Th1 and Th2 subsets: regulation of differentiation and the role in protection and immunopathology. Int. Arch. Allergy Immunol. 98, 279–285.

Romani, N., Gruner, S., Brang, D., Kampgen, E., Lenz, A., Trockenbacher, B., Konwalinka, G., Fritsch, P. O., Steinman, R. M., and Schuler, G. (1994). Proliferating dendritic cell progenitors in human blood. J. Exp. Med. 180, 83–93.

Rosenfield, M. E., Butler, S., Ord, V. A., Lipton, B. A., Dyer, C. A., Curtiss, L. K., Palinski, W., and Witztum, J. L. (1993). Abundant expression of apoprotein E by macrophages in human and rabbit atherosclerosis. Arterioscler. Thromb. 13, 1382–1389.

Rossini, A. A., Greiner, D. L., Friedman, H. P., and Mordes, J. P. (1993). Immunopathogenesis of diabetes mellitus. Diabetes Rev. 1, 43–75.

Rulifson, I. C., Sperling, A., Fields, P. E., Fitch, F. W., Bluestone, J. A. (1997) CD28 costimulation promotes the production of the Th2 cytokines. J. Immunol., Jan. 15, 158(2):658–65.

Salomon, B., Cohen, J. L., Masurier, C., and Klatzmann, D. (1998). Three populations of mouse lymph node dendritic cells with different origins and dynamics. J. Immunol. 160, 708–717.

Santiago-Schwarz, F., Belilos, E., Diamond, B., and Carsons, S. E. (1992). TNF in combination with GM-CSF enhances the differentiation of neonatal cord blood stem cells into dendritic cells and macrophages. J. Leukocyte Biol. 52, 274–281.

Scheicher, C., Mehlig, M., Zecher, R., and Reske, K. (1992). Dendritic cells from mouse bone marrow: in vitro differentiation using low doses of recombinant granulocyte/macrophage CSF. J. Immunol. Methods 154, 253–264.

Schuler, G., Thurner, B., and Romani, N. (1997). Dendritic cells: from ignored cells to major players in T-cell-mediated immunity. Int Arch Allergy Immunol. 112, 317–322.

Seder, R. A., Paul, W. E., Davis, M. M., Fazekas, de St. Groth, B. (1992). The presence of interleukin-4 during in vitro priming determines the lymphokine-producing potential of CD4+ T cells from T cell receptor transgenic mice. J. Exp. Med. 176, 1091–1098.

Seder, R. A., Gazzinelli, R., Sher, A., and Paul, W. E. (1993). IL-12 acts directly on CD4+ T cells to enhance priming for IFNγ production and diminishes IL-4 inhibition of such priming. Proc. Natl. Acad. Sci. USA 90, 10188–10192.

Serreze, D. V., Leiter, E. H. (1988) Defective activation of T suppressor cell function in nonobese diabetic mice. J. Immunol. 140:3801–3807.

Serreze, D. V., Gaskins, H. R., Leiter, E. H. (1993) Defects in the differentiation and funciton of antigen-presenting cells in NOD/LT mice. J. Immunol. 150:2534–2543.

Steinman, R. M., Pack, M., and Inaba, K. (1997). Dendritic cells in the T-cell areas of lymphoid organs. Imm. Reviews 156, 25–37.

Steinbrink, K., Wolfl, M., Jonuleit, H., Knop, Jurgen, and Enk, A. (1997). Induction of tolerance by IL-10-treated dendritic cells. J. lmmunol. 159, 4772–4780.

Steinman, R. M. 1991. The dendritic cell system and its role in immunogenicity. Ann. Rev. Immunol. 9:271–96.

Steptoe, R. J., and Thompson, A. W. (1996). Dendritic cells and tolerance induction. Clin. Exp. Immunol. 105, 397–402.

Stewart, T. A., Hultgren, B., Huang, X., Pitts-Meek, S., Hully, J., and MacLachlan, N. J. (1993). Induction of type I diabetes by interferon-a in transgenic mice. Science 260, 1942–1946.

Thompson, C. B. (1995). Distinct roles for the costimulatory ligands B7-1 and B7-2 in T helper cell differentiation? Cell 81, 979–982.

Trembleau, S., Penna, G., Bosi, E., Mortara, A., Gately, M. K., and Adorini, L. (1995). Interleukin-12 administration induces T helper type 1 and accelerates disease in NOD mice. J. Exp. Med. 181, 817–821.

Trinchieri, G. (1995). Interleukin-12: a proinflammatory cytokine with immunoregulatory functions that bridge innate resistance and antigen-specific adaptive immunity. Annu. Rev. Immunol. 13, 251–276.

Vogel, T., Guo, N. H., Guy, R., Drezlich, N., Krutzsch, H. C., Blake, D. A., Panet, A., and Roberts, D. D. (1994). Apolipoprotein E: a potent inhibitor of endothelial and tumour cell proliferation. J Cell Biochem. 54, 299–308.

Wilson, S. B., Kent, S. C., Patton, K. T., Orban, T., Jackson, R. A., Exley, M., Porcelli, S., Schatz, D. A., Atkinson, M. A., Balk, S. P., Strominger, J. L., and Hafler, D. A. (1998) Extreme Th1 bias of invariant V-alpha-24J-alpha-Q T cells in type 1 diabetes (Letter to Nature). Nature 391:177-##.

Wong, B. R., Josien, R., Lee, S. Y., Sauter, B., Li, H.-L., Steinman, R. M., and Choi, Y. (1997). TRANCE (tumor necrosis factor-related activation-induced cytokine), a new TNF family member predominantly expressed in T cells, is a dendritic cell-specific survival factor. J. Exp. Med. 186, 2075–2080.

Zipris, D., Crow, A., and Delovitch, T. L. (1991a). Altered thymic and peripheral T lymphocyte repertoire precedes the onset of diabetes in NOD mice. Diabetes 40, 429–435.

Zipris, D., Lazarus, A. H., Crow, A., Hadzija, M., and Delovitch, T. L. (1991b). Defective thymic T cells activation by Concavalin A and anti-CD3 in autoimmune nonobese diabetic mice. Evidence for thymic T cell anergy that correlates with the onset of insulitis. J. Immunol. 146, 3763–3771.

We claim:

1. A method of immune modulation comprising administering an effective amount of an apoEp1.B peptide or a nucleic acid encoding an apoEp1.B peptide to a cell or animal in need thereof.

2. A method according to claim 1 wherein the immune modulation is the induction of cell differentiation.

3. A method according to claim 2 wherein the method induces differentiation of a monocyte to a dendritic cell.

4. A method according to claim 2 wherein the cell is a tumor cell.

5. A method according to claim 1 wherein the immune modulation is the induction of immune tolerance.

6. A method according to claim 1 wherein the immune modulation is the inhibition of inflammation.

7. A method according to claim 6 wherein the immune modulation is the inhibition atherosclerotic plaque formation.

8. A method according to claim 1 wherein the immune modulation is the treatment of an autoimmune disease.

9. A method according to claim 8 wherein the autoimmune disease is diabetes.

10. A method according to claim 1 wherein the immune modulation is the induction of an immune response.

11. A method according to claim 10 further comprising administering a cytokine to the cell or animal in need thereof.

12. A method according claim 1 wherein said peptide is administered to a cell in vitro.

13. A method according to claim 1 wherein the apoEp1.B peptide (1) has the amino acid sequence TQQIRLQAEIFQAR (amino acids 239–252) (SEQ.ID.NO.:1); (2) is an analog of (1) wherein the modification occurs in one of amino acids 239–243; (3) is a fragment of (1) or (2) wherein said fragment comprises amino acids 240–252; or (4) is an elongation of (1), (2) or (3) wherein the elongation contains an additional amino acid at position 238.

14. A method according to claim 1 wherein the apoEp1.B peptide (1) has the amino acid sequence AQQIRLQAEAFQAR (amino acids 239–252) (SEQ.ID.NO.:2); (2) is an analog of (1) wherein the modification occurs in one of amino acids 239–243; (3) is a fragment of (1) or (2) wherein said fragment comprises amino acids 240–252; or (4) is an elongation of (1), (2) or (3) wherein the elongation contains an additional amino acid at position 238.

15. A method according to claim 1 wherein the apoEp1.B peptide has the amino acid sequence TAQIRLQAEIFQAR (SEQ.ID.NO.:3).

16. A method according to claim 1 wherein the apoEp1.B peptide has the amino acid sequence TQAIRLQAEIFQAR (SEQ.ID.NO.:4).

17. A method according to claim 1 wherein the apoEp1.B peptide has the amino acid sequence TQQARLQAEIFQAR (SEQ.ID.NO.:5).

18. A method according to claim 1 wherein the apoEp1.B peptide has the amino acid sequence TQQIALQAEIFQAR (SEQ.ID.NO.:6).

19. A method according to claim 1 wherein the apoEp1.B peptide has the amino acid sequence QTQQIRLQAEIFQAR (SEQ.ID.NO.:7).

20. A method according to claim 1 wherein the apoEp1.B peptide has the amino acid sequence QQIRLQAEIFQAR (SEQ.ID.NO.:8).

21. A method of inducing tolerogenic dendritic cells comprising administering an effective amount of an apoEp1.B peptide or a nucleic acid encoding an apoEp1.B peptide to a cell or animal in need thereof.

22. A method according to claim 21 wherein the apoEp1.B peptide (1) has the amino acid sequence TQQIRLQAEIFQAR (amino acids 239–252) (SEQ.ID.NO.:1); (2) is an analog of (1) wherein the modification occurs in one of amino acids 239–243; (3) is a fragment of (1) or (2) wherein said fragment comprises amino acids 240–252 or (4) is an elongation of (1), (2) or (3) wherein the elongation contains an additional amino acid at position 238.

23. A method according to claim 21 wherein the apoEp1.B peptide (1) has the amino acid sequence AQQIRLQAEAFQAR (amino acids 239–252) (SEQ.ID.NO.:2); (2) is an analog of (1) wherein the modification occurs in one of amino acids 239–243; (3) is a fragment of (1) or (2) wherein said fragment comprises amino acids 240–252 or (4) is an elongation of (1), (2) or (3) wherein the elongation contains an additional amino acid at position 238.

24. A method according to claim 21 wherein the apoEp1.B peptide has the amino acid sequence TAQIRLQAEIFQAR (SEQ.ID.NO.:3).

25. A method according to claim 21 wherein the apoEp1.B peptide has the amino acid sequence TQAIRLQAEIFQAR (SEQ.ID.NO.:4).

26. A method according to claim 21 wherein the apoEp1.B peptide has the amino acid sequence TQQARLQAEIFQAR (SEQ.ID.NO.:5).

27. A method according to claim 21 wherein the apoEp1.B peptide has the amino acid sequence TQQIALQAEIFQAR (SEQ.ID.NO.:6).

28. A method according to claim 21 wherein the apoEp1.B peptide has the amino acid sequence QTQQIRLQAEIFQAR (SEQ.ID.NO.:7).

29. A method according to claim 21 wherein the apoEp1.B peptide has the amino acid sequence QQIRLQAEIFQAR (SEQ.ID.NO.:8).

30. A method of treating a tumor comprising administering an effective amount of an apEp1.B peptide or a nucleic acid encoding an apoEp1.B peptide to an animal in need thereof.

31. A method according to claim 30 wherein the apoEp1.B peptide (1) has the amino acid sequence TQQIRLQAEIFQAR (amino acids 239–252) (SEQ.ID.NO.:1); (2) is an analog of (1) wherein the modification occurs in one of amino acids 239–243; (3) is a fragment of (1) or (2) wherein said fragment comprises amino acids 240–252 or (4) is an elongation of (1), (2) or (3) wherein the elongation contains an additional amino acid at position 238.

32. (New) A method according to claim 30 wherein the apoEp1.B peptide (1) has the amino acid sequence AQQIRLQAEAFQAR (amino acids 239–252) (SEQ.ID.NO.:2); (2) is an analog of (1) wherein the modification occurs in one of amino acids 239–243; (3) is a fragment of (1) or (2) wherein said fragment comprises amino acids 240–252 or (4) is an elongation of (1), (2) or (3) wherein the elongation contains an additional amino acid at position 238.

33. A method according to claim 30 wherein the apoEp1.B peptide has the amino acid sequence TAQIRLQAEIFQAR (SEQ.ID.NO.:3).

34. A method according to claim 13 wherein the apoEp1.B peptide has the amino acid sequence TQAIRLQAEIFQAR (SEQ.ID.NO.:4).

35. A method according to claim 30 wherein the apoEp1.B peptide has the amino acid sequence TQQARLQAEIFQAR (SEQ.ID.NO.:5).

36. A method according to claims 13 wherein the apoEp1.B peptide has the amino acid sequence TQQIALQAEIFQAR (SEQ.ID.NO.:6).

37. A method according to claim 30 wherein the apoEp1.B peptide has the amino acid sequence QTQQIRLQAEIFQAR (SEQ.ID.NO.:7).

38. A method according to claim 13 wherein the apoEp1.B peptide has the no acid sequence QQIRLQAEIFQAR (SEQ.ID.NO.:8).

39. A pharmaceutical composition for modulating an immune response comprising an apoEp1.B peptide or a nucleic acid encoding an apoEp1.B peptic in admixture with a suitable diluent or carrier.

40. A pharmaceutical composition according to claim 39 wherein the apoEp1.B peptide (1) has the amino acid sequence TQQIRLQAEIFQAR (amino acids 239–252) (SEQ.ID.NO.:1); (2) is an analog of (1) wherein the modification occurs in one of amino acids 239–243; (3) is a fragment of (1) or (2) wherein said fragment comprises amino acids 240–252; or (4) is an elongation of (1), (2) or (3) wherein the elongation contains an additional amino acid at position 238.

41. A pharmaceutical composition according to claim 39 wherein the apoEp1.B peptide (1) has the amino acid sequence AQQIRLQAEAFQAR (amino acids 239–252) (SEQ.ID.NO.:2); (2) is an analog of (1) wherein the modification occurs in one of amino acids 239–243; (3) is a fragment of (1) or (2) wherein said fragment comprises amino acids 240–252; or (4) is an elongation of (1), (2) or (3) wherein the elongation contains an additional amino acid at position 238.

42. A pharmaceutical composition according to claim 39 wherein the apoEp1.B peptide has the amino acid sequence TAQIRLQAEIFQAR (SEQ.ID.NO.:3).

43. A pharmaceutical composition according to claim 39 wherein the apoEp1.B peptide has the amino acid sequence TQAIRLQAEIFQAR (SEQ.ID.NO.:4).

44. A pharmaceutical composition according to claim 39 wherein the apoEp1.B peptide has the amino acid sequence TQQARLQAEIFQAR (SEQ.ID.NO.:5).

45. A pharmaceutical composition according to claim 39 wherein the apoEp1.B peptide has the amino acid sequence TQQIALQAEIFQAR (SEQ.ID.NO.:6).

46. A pharmaceutical composition according to claim 39 wherein the apoEp1.B peptide has the amino acid sequence QTQQIRLQAEIFQAR (SEQ.ID.NO.:7).

47. A pharmaceutical composition according to claim 39 wherein the apoEp1.B peptide has the amino acid sequence QQIRLQAEIFQAR (SEQ.ID.NO.:8).

48. A pharmaceutical composition according to claim 39 further comprising a cytokine.

49. An isolated apoEp1.B peptide (1) having the amino acid sequence AQQIRLQAEAFQAR (amino acids 239–252) (SEQ.ID.NO.:2); (2) is an analog of (1) wherein the modification occurs in one of amino acids 239–243; (3) is a fragment of (1) or (2) wherein said fragment comprises amino acids 240–252; or (4) is an elongation of (1), (2) or (3) wherein the elongation contains an additional amino acid at position 238.

50. An isolated apoEp1.B peptide having the amino acid sequence TAQIRLQAEIFQAR (SEQ.ID.NO.:3).

51. An isolated apoEp1.B peptide having the amino acid sequence TQAIRLQAEIFQAR (SEQ.ID.NO.:4).

52. An isolated apoEp1.B peptide having the amino acid sequence TQQARLQAEIFQAR (SEQ.ID.NO.:5).

53. An isolated apoEp1.B peptide having the amino acid sequence TQQIALQAEIFQAR (SEQ.ID.NO.:6).

54. An isolated apoEp1.B peptide having the amino acid sequence QTQQIRLQAEIFQAR (SEQ.ID.NO.:7).

55. An isolated apoEp1.B peptide having the amino acid sequence QQIRLQAEIFQAR (SEQ.ID.NO.:8).

* * * * *

SEQUENCE LISTING

```
<160> NUMBER OF SEQ ID NOS: 20

<210> SEQ ID NO 1
<211> LENGTH: 14
<212> TYPE: PRT
<213> ORGANISM: Murine

<400> SEQUENCE: 1

Thr Gln Gln Ile Arg Leu Gln Ala Glu Ile Phe Gln Ala Arg
 1               5                  10

<210> SEQ ID NO 2
<211> LENGTH: 14
<212> TYPE: PRT
<213> ORGANISM: Homo sapiens

<400> SEQUENCE: 2

Ala Gln Gln Ile Arg Leu Gln Ala Glu Ala Phe Gln Ala Arg
```

1               5                    10

<210> SEQ ID NO 3
<211> LENGTH: 14
<212> TYPE: PRT
<213> ORGANISM: Artificial Sequence
<220> FEATURE:
<223> OTHER INFORMATION: apoEp1.B A240

<400> SEQUENCE: 3

Thr Ala Gln Ile Arg Leu Gln Ala Glu Ile Phe Gln Ala Arg
1               5                    10

<210> SEQ ID NO 4
<211> LENGTH: 14
<212> TYPE: PRT
<213> ORGANISM: Artificial Sequence
<220> FEATURE:
<223> OTHER INFORMATION: apoEp1.B A241

<400> SEQUENCE: 4

Thr Gln Ala Ile Arg Leu Gln Ala Glu Ile Phe Gln Ala Arg
1               5                    10

<210> SEQ ID NO 5
<211> LENGTH: 14
<212> TYPE: PRT
<213> ORGANISM: Artificial Sequence
<220> FEATURE:
<223> OTHER INFORMATION: apoEp1.B A242

<400> SEQUENCE: 5

Thr Gln Gln Ala Arg Leu Gln Ala Glu Ile Phe Gln Ala Arg
1               5                    10

<210> SEQ ID NO 6
<211> LENGTH: 14
<212> TYPE: PRT
<213> ORGANISM: Artificial Sequence
<220> FEATURE:
<223> OTHER INFORMATION: apoEp1.B A243

<400> SEQUENCE: 6

Thr Gln Gln Ile Ala Leu Gln Ala Glu Ile Phe Gln Ala Arg
1               5                    10

<210> SEQ ID NO 7
<211> LENGTH: 15
<212> TYPE: PRT
<213> ORGANISM: Murine

<400> SEQUENCE: 7

Gln Thr Gln Gln Ile Arg Leu Gln Ala Glu Ile Phe Gln Ala Arg
1               5                    10                  15

<210> SEQ ID NO 8
<211> LENGTH: 13
<212> TYPE: PRT
<213> ORGANISM: Murine

<400> SEQUENCE: 8

Gln Gln Ile Arg Leu Gln Ala Glu Ile Phe Gln Ala Arg
1               5                    10

<210> SEQ ID NO 9
<211> LENGTH: 17

```
<212> TYPE: PRT
<213> ORGANISM: Murine

<400> SEQUENCE: 9

Glu Glu Gln Thr Gln Gln Ile Arg Leu Gln Ala Glu Ile Phe Gln Ala
1               5                   10                  15
Arg

<210> SEQ ID NO 10
<211> LENGTH: 16
<212> TYPE: PRT
<213> ORGANISM: Murine

<400> SEQUENCE: 10

Glu Gln Thr Gln Gln Ile Arg Leu Gln Ala Glu Ile Phe Gln Ala Arg
1               5                   10                  15

<210> SEQ ID NO 11
<211> LENGTH: 12
<212> TYPE: PRT
<213> ORGANISM: Murine

<400> SEQUENCE: 11

Gln Ile Arg Leu Gln Ala Glu Ile Phe Gln Ala Arg
1               5                   10

<210> SEQ ID NO 12
<211> LENGTH: 14
<212> TYPE: PRT
<213> ORGANISM: Artificial Sequence
<220> FEATURE:
<223> OTHER INFORMATION: apoEp1.B A244

<400> SEQUENCE: 12

Thr Gln Gln Ile Arg Ala Gln Ala Glu Ile Phe Gln Ala Arg
1               5                   10

<210> SEQ ID NO 13
<211> LENGTH: 14
<212> TYPE: PRT
<213> ORGANISM: Artificial Sequence
<220> FEATURE:
<223> OTHER INFORMATION: apoEp1.B A245

<400> SEQUENCE: 13

Thr Gln Gln Ile Arg Leu Ala Ala Glu Ile Phe Gln Ala Arg
1               5                   10

<210> SEQ ID NO 14
<211> LENGTH: 14
<212> TYPE: PRT
<213> ORGANISM: Artificial Sequence
<220> FEATURE:
<223> OTHER INFORMATION: aoEp1.B A247

<400> SEQUENCE: 14

Thr Gln Gln Ile Arg Leu Gln Ala Ala Ile Phe Gln Ala Arg
1               5                   10

<210> SEQ ID NO 15
<211> LENGTH: 14
<212> TYPE: PRT
<213> ORGANISM: Artificial Sequence
<220> FEATURE:
<223> OTHER INFORMATION: apoEp1.B A248
```

```
<400> SEQUENCE: 15

Thr Gln Gln Ile Arg Leu Gln Ala Glu Ala Phe Gln Ala Arg
1               5                   10

<210> SEQ ID NO 16
<211> LENGTH: 14
<212> TYPE: PRT
<213> ORGANISM: Artificial Sequence
<220> FEATURE:
<223> OTHER INFORMATION: apoEp1.B A249

<400> SEQUENCE: 16

Thr Gln Gln Ile Arg Leu Gln Ala Glu Ile Ala Gln Ala Arg
1               5                   10

<210> SEQ ID NO 17
<211> LENGTH: 14
<212> TYPE: PRT
<213> ORGANISM: Artificial Sequence
<220> FEATURE:
<223> OTHER INFORMATION: apoEp1.B A250

<400> SEQUENCE: 17

Thr Gln Gln Ile Arg Leu Gln Ala Glu Ile Phe Ala Ala Arg
1               5                   10

<210> SEQ ID NO 18
<211> LENGTH: 14
<212> TYPE: PRT
<213> ORGANISM: Artificial Sequence
<220> FEATURE:
<223> OTHER INFORMATION: apoEp1.B A239, 240

<400> SEQUENCE: 18

Ala Ala Gln Ile Arg Leu Gln Ala Glu Ile Phe Gln Ala Arg
1               5                   10

<210> SEQ ID NO 19
<211> LENGTH: 14
<212> TYPE: PRT
<213> ORGANISM: Artificial Sequence
<220> FEATURE:
<223> OTHER INFORMATION: apoEp1.B A240, 241

<400> SEQUENCE: 19

Thr Ala Ala Ile Arg Leu Gln Ala Glu Ile Phe Gln Ala Arg
1               5                   10

<210> SEQ ID NO 20
<211> LENGTH: 14
<212> TYPE: PRT
<213> ORGANISM: Artificial Sequence
<220> FEATURE:
<223> OTHER INFORMATION: apoEp1.B A239-241

<400> SEQUENCE: 20

Ala Ala Ala Ile Arg Leu Gln Ala Glu Ile Phe Gln Ala Arg
1               5                   10
```